US009738668B2

(12) United States Patent
Yan et al.

(10) Patent No.: US 9,738,668 B2
(45) Date of Patent: *Aug. 22, 2017

(54) PHOSPHONATE DERIVATIVES AND METHODS OF USE THEREOF IN THE TREATMENT OF ALZHEIMER'S DISEASE

(71) Applicant: University of Kansas, Lawrence, KS (US)

(72) Inventors: ShiDu Yan, Lawrence, KS (US); Koteswara Rao Valasani, Kadapa (IN)

(73) Assignee: University of Kansas, Lawrence, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/163,275

(22) Filed: May 24, 2016

(65) Prior Publication Data

US 2016/0263133 A1  Sep. 15, 2016

Related U.S. Application Data

(63) Continuation of application No. 14/539,050, filed on Nov. 12, 2014, now Pat. No. 9,346,839, which is a continuation-in-part of application No. PCT/US2013/040707, filed on May 13, 2013.

(60) Provisional application No. 61/646,548, filed on May 14, 2012.

(51) Int. Cl.
*C07F 9/6541* (2006.01)
*C07F 9/6558* (2006.01)
*C07F 9/40* (2006.01)
*A61K 31/675* (2006.01)

(52) U.S. Cl.
CPC .......... *C07F 9/6541* (2013.01); *A61K 31/675* (2013.01); *C07F 9/4056* (2013.01); *C07F 9/65583* (2013.01); *C07F 9/65586* (2013.01)

(58) Field of Classification Search
CPC .................................................. C07F 9/6541
See application file for complete search history.

(56) References Cited

U.S. PATENT DOCUMENTS

| | | | |
|---|---|---|---|
| 3,954,860 A | 5/1976 | Birum | 564/15 |
| 4,036,913 A | 7/1977 | Birum | 260/938 |
| 5,424,303 A * | 6/1995 | Phan | C07F 9/3882 514/89 |
| 9,346,839 B2 * | 5/2016 | Yan | C07F 9/54 |
| 2008/0312191 A1 | 12/2008 | Augustyns et al. | 514/119 |

OTHER PUBLICATIONS

Wang et al. "Synthesis and anti-tobacco mosaic virus activity of O,O'-dialkyl-_-(substituted benzothiazol-2-yl)amino-(substituted phenylmethyl)phosphonate" Youji Huaxue (2007), 27(2), 279-284.*

Casperson et al. "Mitochondrial Aβ: a potential focal point for neuronal metabolic dysfunction in Alzheimer's disease" The FASEB Journal FJ Express 2005 19(14):2040-2041.
Chen et al. "Role of Mitochondrial Amyloid-β in Alzheimer's Disease" Journal of Alzheimer's Disease 2010 20:S569-S578.
Devi et al. "Accumulation of Amyloid Precursor Protein in the Mitochondrial Import Channels of Human Alzheimer's Disease Brain Is Associated with Mitochondrial Dysfunction" The Journal of Neuroscience 2006 26(35):9057-9068.
Du et al. "Cyclophilin D deficiency improves mitochondrial function and learning/memory in aging Alzheimer disease mouse model" Neurobiology of Aging 2011 32:398-406.
Du et al. "Synaptic Mitochondrial Pathology in Alzheimer's Disease" Antioxidants & Redox Signaling 2012 16(12):1467-1475.
Du et al. "Cyclophilin D deficiency attenuates mitochondrial and neuronal perturbation and ameliorates learning and memory in Alzheimer's disease" Nature Medicine 2008 14(10):1097-1105.
Du et al. "Early deficits in synaptic mitochondria in an Alzheimer's disease mouse model" Proceedings of the National Academy of Sciences USA 2010 107 (43):18670-18675.
Hauptmann et al. "Mitochondrial dysfunction: An early event in Alzheimer pathology accumulates with age in AD transgenic mice" Neurobiology of Aging 2009 30:1574-1586.
Higuchi et al. "Pro-drugs as Novel Drug Delivery Systems" American Chemical Society Symposium Series Washington D.C. 1975.
Kim et al. "A High-Throughput Screen for Compounds That Inhibit Aggregation of the Alzheimer's Peptide" ACS Chemical Biology 2006 1(7):461-469.
Lin et al. "Alzheimer's APP mangles mitochondria" Nature Medicine 2006 12(11):1241-1243.
Lustbader et al. "ABAD Directly Links Aβ to Mitochondrial Toxicity in Alzheimer's Disease" Science 2004 304:448-452.
Manczak et al. "Mitochondria are a direct site of Aβ accumulation in Alzheimer's disease neurons: implications for free radical generation and oxidative damage in disease progression" Human Molecular Genetics 2006 15(9):1437-1449.
Marques et al. "Molecular dynamics simulations of the amyloid-beta binding alcohol dehydrogenase (ABAD) enzyme" Bioorganic & Medicinal Chemistry 2008 16:9511-9518.
Mayer et al. "Characterization of Ligand Binding by Saturation Transfer Difference NMR Spectroscopy" Angewandte Chemie International Edition 1999 38(12)1784-1788.
Reddy et al. "Amyloid beta, mitochondrial dysfunction and synaptic damage: implications for cognitive decline in aging and Alzheimer's disease" Trends in Molecular Medicine 2008 14(2):45-53.
Sato et al. "Signal Peptide Peptidase: Biochemical Properties and Modulation by Nonsteroidal Anti-inflammatory Drugs" Biochemistry 2006 45:8649-8656.
Takuma et al. "ABAD enhances Aβ-induced cell stress via mitochondrial dysfunction" The FASEB Journal FJ Express 2005 598(19):597-598.
Wang et al. "Amyloid-overproduction causes abnormal mitochondrial dynamics via differential modulation of mitochondrial fission/fusion proteins" Proceedings of the National Academy of Sciences USA 2008 105(49):19318-19323.

(Continued)

*Primary Examiner* — Joseph Kosack
(74) *Attorney, Agent, or Firm* — Licata & Tyrrell P.C.

(57) ABSTRACT

Benzothiazole phosphonate analogs and methods of using the same to inhibit the activity of Amyloid Binding Alcohol Dehydrogenase and in the amelioration or treatment of Alzheimer's disease are provided.

5 Claims, 11 Drawing Sheets

(56) References Cited

OTHER PUBLICATIONS

Xie et al. "Identification of small-molecule inhibitors of the Aβ-ABAD interaction" Bioorganic & Medicinal Chemistry Letters 2006 16:4657-4660.

Yao et al. "Mitochondrial bioenergetic deficit precedes Alzheimer's pathology in female mouse model of Alzheimer's disease" Proceedings of the National Academy of Sciences USA 2009 106 (34):14670-14675.

Extended European Search Report and Written Opinion dated Feb. 9, 2016 from EP 13791199.6 filed May 13, 2013.

Wang et al. "A Convenient Synthesis of N-t-Butyl-N' Aminocarbonyl-N-(Substituted)Benzoyl-hydrazine Containing α-Aminoalkylphosphoneate Groups in a One-Pot Procedure" Heteroatom Chemistry 2001 12(2):68-72.

Kuzdin and Stec "Synthesis of 1-Aminoalkanephosphonase via Thioureidoalkanephosphoanates" 1978, retrieved from internet (url:https://www.thieme-connect.de/products/ejournals/pdf/10. 1055/s-1978-24787.pdf) pp. 469-472, Compound 41 in Table 1, Compound 7 in Scheme C and Procedure C on p. 472.

Birum, G.H. "Urylenediphosphonates. A General Method for the Synthesis of α-Ureidophosphonates and Related Structures" J. Org. Chem. 1974 39(2):209-213.

Kozhushko et al. Database Reaxys Online 1983 XP002753602, Database Accession No. 2208268.

Jin et al. "Synthesis, X-ray Crystallographic Analysis, and Antitumor Activity of N-(benzothiazole-2-yl)-1-(fluorophenyl)-O,O-dialkyl-60 -aminophosphonates" Bioorganic & Medicinal Chemistry Letters 2006 16:1537-1543.

Rao et al. "Microwave Assisted One-pot Synthesis of Novel α-Aminophosphonates and Their Biological Activity" Bull. Korean Soc. 2010 31(7):1863-1868.

Reddy et al. "PEG-SO₃H Catalyzed Synthesis and Cytotoxicity of α-aminophosphonates" European J. Med. Chemistry 2012 47:553-559.

Kissinger et al. "Crystal Structure of Human ADAD/HSD10 with a Bound Inhibitor: Implications for Design of Alzheimer's Disease Therapeutics" J. Mol. Biol. 2004 342:943-952.

Jin et al. "Synthesis, X-ray Crystallographic Analysis, and Antitumor Activity of N-(benzothiazole-2-yl)-1-(fluorophenyl)-O,O-dialkyl-α-aminophosphonates" Database CA Online Chemical Abstracts Service, Columbus, OH, XP002753624 Database Assession No. 2006:128492 abstract.

Song et al. "Synthesis, Structure and Antitumor Activity of α-substituted aminofluoroarylphosphonate Derivatives" 2005 XP002753625 Database Accession No. 2005:943279 abstract.

Lu et al. "Chiral Separation of Novel α-Aminophosphonates Containing a Benzothiazole Moiety by Liquid Chromatography Using an Amylose Stationary Phase" Database CA Online Chemical Abstracts Service, Columbus, OH 2008 XP002753626 Database Accession No. 2008:1308479 abstract.

Song et al. "Preparation of dialkyl 1-(Substituted benzothialzol-2-yl)amino-1-(substituted phenyl)methyl phosphonate Derivatives and their Antiviral and Antitumor Activities" 2006 XP002753627 Database Accession No. 2006:584798 abstract.

Hong et al. "Dimethly[ (4-fluorophenyl)(6-methoxybenzothiazol-2-ylamino)methyl ])phosphonate" 2009 XP002753628 Database Accession No. 2009:677858 abstract.

Koteswara et al. "Structure-Based Design and Synthesis of Benzothiazole Phosphonate Analogues with Inhibitors of Human ABAD-Aβ for Treatment of Alzeheimer's Disease" Chem. Biol. Drug Des. 2013 81:238-249.

Zhang et al. "Lipophilicity determination of N-(benzothiazol-2-yl)-α-amino alkyl phosphonic diesters by RP-HPLC and RP-HPTLC" CAS Accession No. 2000:859668 from Chinese Jounral of Chemistry 2000 18(6):872-876.

Office Communication dated Dec. 18, 2014 from U.S. Appl. No. 14/539,050, filed Nov. 12, 2014.

Office Communication dated Aug. 13, 2015 from U.S. Appl. No. 14/539,050, filed Nov. 12, 2014.

Office Communication dated Nov. 25, 2015 from U.S. Appl. No. 14/539,050, filed Nov. 12, 2014.

Office Communication dated Feb. 18, 2016 from U.S. Appl. No. 14/539,050, filed Nov. 12, 2014.

Office Communication dated Apr. 21, 2016 from U.S. Appl. No. 14/539,050, filed Nov. 12, 2014.

* cited by examiner

PHOSPHONATE DERIVATIVES AND METHODS OF USE THEREOF IN THE TREATMENT OF ALZHEIMER'S DISEASE

INTRODUCTION

This application is a continuation of U.S. Ser. No. 14/539,050 filed Nov. 12, 2014, which is a continuation-in-part application of PCT/US2013/040707, filed May 13, 2013, which claims the benefit of priority from U.S. Patent Application Ser. No. 61/646,548, filed May 14, 2012, the contents of each of which is incorporated herein by reference in their entireties.

This invention was made with government support under Grant Nos. GM095355, AG037319 and AG017409 awarded by the National Institutes of Health. The government has certain rights in the invention.

BACKGROUND OF THE INVENTION

Alzheimer's disease (AD) is one of the most common dementia showing slowly progressive cognitive decline. Alzheimer's brain is characterized by accumulation of amyloid beta peptide (Aβ) and the formation of neurofibrillary tangles. AP plays a central role in the development of AD pathology and contributes to neuronal, synaptic, and cognitive malfunction. Mitochondrial and synaptic dysfunction is an early pathological feature of Alzheimer's disease brain (Du, et al. (2010) *Proc. Natl. Acad. Sci. USA* 107:18670; Du, et al. (2011) *Antioxid. Redox Signal.* doi:10.1089/ars.2011.4277; Chen, et al. (2010) *J. Alzheimer's Dis.* 20 Suppl 2: 5569; Caspersen, et al. (2005) *FASEB J.* 19:2040; Reddy, et al. (2008) *Trends Mol. Med.* 14:45; Lin & Beal (2006) *Nat. Med.* 12:1241). Studies have highlighted the significance of mitochondrial Aβ accumulation and synaptic mitochondrial dysfunction. Aβ progressively accumulates in synaptic mitochondria and impairs mitochondrial structure and function including membrane potential, membrane permeability transition pore, respiration, energy metabolism, oxidative stress, mitochondrial dynamics, and calcium homeostasis (Caspersen, et al. (2005) supra; Du, et al. (2008) *Nat. Med.* 14:1097; Manczak, et al. (2006) *Hum. Mol. Genet.* 15:1437; Lustbader, et al. (2004) *Science* 304: 448; Devi, et al. (2006) *J. Neurosci.* 26:9057; Eckert, et al. (2008) *Neurodegen. Dis.* 5:157; Hauptmann, et al. (2009) *Neurobiol. Aging* 30:1574; Du, et al. (2011) *Neurobiol. Aging* 32:398; Yao, et al. (2009) *Proc. Natl. Acad. Sci. USA* 106:14670; Yao, et al. (2011) *J. Neurosci.* 31:2313; Manczak, et al. (2011) *Hum. Mol. Genet.* 20:2495; Wang, et al. (2008) *Proc. Natl. Acad. Sci. USA* 105:19318). Thus, strategies that suppress/attenuate Aβ-induced mitochondrial toxicity in addition to Aβ levels in the brain and improve cognitive function are critical for preventing and/or halting Alzheimer disease (AD). Development of Aβ inhibitors or blocking the Aβ production one approach for prevention and treatment of AD.

Potent γ-secretase inhibitors are available to eliminate Aβ production. Unfortunately, subchronic dosing of rodents with γ-secretase inhibitors has caused abnormalities in the gastrointestinal tract, thymus, and spleen. These abnormalities are mechanism-based toxicities that likely result from the inhibition of the cleavage of Notch by γ-secretase (Sato, et al. (2006) *Biochemistry* 45:8649). These γ-secretase-mediated toxicities raise the critical question of whether an acceptable therapeutic index can be found for γ-secretase inhibitors.

Amyloid binding alcohol dehydrogenase (ABAD), a mitochondrial enzyme, plays a critical role in mitochondrial dysfunction and in the pathogenesis of AD. This enzyme has attracted considerable interest because of its ability to interact with the Aβ. Importantly, interaction of ABAD with Aβ mediates mitochondrial and synaptic dysfunction (Lustbader, et al. (2004) supra). Antagonizing Aβ-ABAD interaction with the ABAD decoy peptide that encompasses the amino residues responsible for Aβ binding to ABAD protects against aberrant mitochondrial and neuronal function and improves learning memory in AD transgenic mice (Yao, et al. (2011) supra; Takuma, et al. (2005) *FASEB J.* 19:597). Furthermore, interception of Aβ-ABAD interaction also significantly reduces mitochondrial and cerebral Aβ accumulation (Yao, et al. (2011) supra). These data suggest that Aβ-ABAD interaction is a potential target of the drug development for treatment of AD.

Inhibitors of the Aβ-ABAD interaction have been developed. For example, Congo red provides 100% inhibition of Aβ binding, whereas thioflavin T exhibits ~20%. However, Congo red exhibits a high level of toxicity and poor cell permeability (Xie, et al. (2006) *Bioorg. Med. Chem. Lett.* 16:4657). Therefore, fluorogenic and radiolabeled derivatives of Congo red and thioflavin T were analyzed. The derivatives did not, however, exhibit an increase in inhibitory activity compared to the parent compounds (Kim, et al. (2006) *ACS Chem. Biol.* 1:461-469). Benzothiazoles such as fentizole were also shown to exhibit inhibitory activity (Xie, et al. (2006) supra). In particular, AG18051 was identified as a potent inhibitor of ABAD ($IC_{50}$ of 92 nM; Marques, et al. (2008) *Bioorg. Med. Chem.* 16:9511-9518).

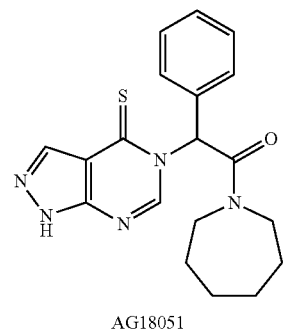 [SMILES: O=C(C(c1ccccc1)n1cnc2[nH]ncc2c1=S)N1CCCCCC1]

AG18051

However, these known inhibitors of Aβ-ABAD interaction have disadvantages including low solubility, inability to cross the blood brain barrier (BBB), high toxicity, and/or low cell permeability.

SUMMARY OF THE INVENTION

The present invention is an ABAD inhibitor of Formula I, or a derivative, stereoisomer, tautomer, pharmaceutically acceptable salt, or prodrug thereof,

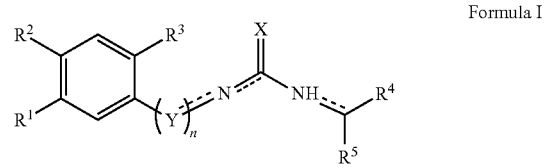

Formula I wherein
n is 0 or 1;
Y is C—R⁶;
X is S or O;
the dashed bonds are independently present or absent;
R¹ and R² are each independently a hydrogen, hydroxyl, halo, alkoxy, or methylcarboxylate group;
R³ is a hydrogen or R³ together with X form a C₅ heteroaryl;
R⁴ and R⁶ are each independently a hydrogen or phosphonate group; and
R⁵ is a substituted or unsubstituted aryl or heteroaryl group;
with the proviso that at least one of R⁴ or R⁶ is a phosphonate group.

In one embodiment, the ABAD inhibitor has the structure of Formula II

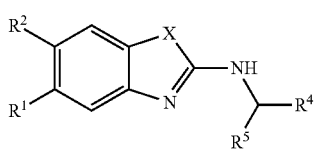

Formula II wherein
X is S or O;
R¹ and R² are each independently a hydrogen, hydroxyl, halo, alkoxy, or methylcarboxylate group;
R⁴ is a phosphonate group; and
R⁵ is a substituted or unsubstituted aryl or heteroaryl group.

In another embodiment, the ABAD inhibitor has the structure of Formula III

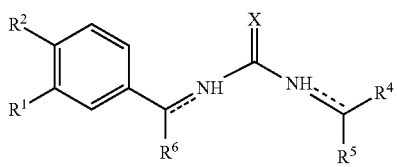

Formula III wherein
X is S or O;
the dashed bonds are independently present or absent;
R¹ and R² are each independently a hydrogen, hydroxyl, halo, alkoxy, or methylcarboxylate group;
R⁴ and R⁶ are each independently a hydrogen or phosphonate group; and
R⁵ is a substituted or unsubstituted aryl or heteroaryl group;
with the proviso that at least one of R⁴ or R⁶ is a phosphonate group.

A pharmaceutical composition containing the ABAD inhibitor and a pharmaceutically acceptable carrier, as well as methods of using the ABAD inhibitor to inhibit the activity of ABAD or ameliorate or treat Alzheimer's Disease are also provided.

BRIEF DESCRIPTION OF THE DRAWINGS

FIG. 3B shows the effect of Compound 8 on the time spent in the second quadrant during the memory test in the water maze probe trial conducted 24 hours after the last training trial of the hidden platform acquisition phase. FIG. 3C shows the effect of Compound 8 on the platform location crossing (the mice crossed the position where the platform was placed during learning sessions). FIG. 3D shows representative swim paths swum during the probe trial for mAPP and Non Tg mice.

FIG. 4B shows the effect of Compound on the time spent in the second quadrant during the memory test in the Morris water maze probe trial conducted hours after the last training trial of the hidden platform acquisition phase. FIG. 4C shows the effect of Compound 8 on the platform location crossing (the mice crossed the position where the platform was placed during learning sessions). FIG. 4D shows representative swim paths swum during the probe trial for mAPP and Non Tg mice.

FIG. 5B shows the residual potentiation from fEPSP slopes occurring over the last 5 minutes of LTP recording.

FIG. 6B shows the effect of Compound 4 on the time spent in the second quadrant during the memory test in the Morris water maze probe trial conducted 4 hours after the last training trial of the hidden platform acquisition phase. FIG. 6C shows the effect of Compound 4 on the platform location crossing (the mice crossed the position where the platform was placed during learning sessions). FIG. 6D shows representative swim paths swum during the probe trial for mAPP and Non Tg mice.

FIG. 7B shows the residual potentiation from fEPSP slopes occurring over the last 5 minutes of LTP recording.

DETAILED DESCRIPTION OF THE INVENTION

Figure 1A:
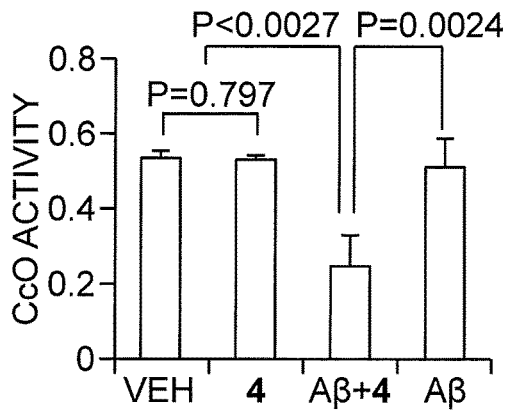
FIGS. 1A-1C show the effect of ABAD inhibitors, Compound 4 (FIG. 1A), Compound 8 (FIG. 1B), and Compound 15 (FIG. 1C), on Aβ-mediated cytochrome c oxidase (CcO) activity. SK-NSH cells were treated with 5 μM oligomer Aβ plus 1 μM of ABAD inhibitor; inhibitor alone; vehicle (VEH) without inhibitor; or Aβ alone. Forty-eight hour later, CcO activity (μmol protein mg$^{-1}$ min$^{-1}$) was measured in cell lysates.

Potent, ligand efficient, selective, and orally efficacious benzothiazole phosphonate analogs have now been identified using structure-based drug design approaches. The structure-activity relationship (SAR) analysis presented herein indicated that the phosphonate moiety was required for inhibitory activity. Inhibitory activity of aminophosphonates was further evaluated in vitro by surface plasma resonance binding assay, enzymatic activity, and mitochondrial swelling assays to validate the effect on mitochondrial function. The instant inhibitors exhibit few adverse effects, increased passage across the BBB, and ameliorate the signs of Alzheimer's disease in an animal model. Given their activity, the instant compounds, as well as derivatives or analogs thereof, find use as antagonists of the Aβ-ABAD interaction, in AD therapeutics and in mitochondrial and synaptic medicine.

Accordingly, the present invention includes an ABAD inhibitor of Formula I, or an analog, stereoisomer, tautomer, pharmaceutically acceptable salt, or prodrug thereof. Compounds of Formula I have the structure:

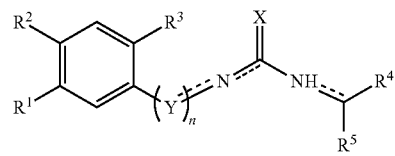

Formula I wherein
n is 0 or 1;
Y is C—R$^6$;
X is S or O;
the dashed bonds are independently present or absent;
R$^1$ and R$^2$ are each independently a hydrogen, hydroxyl, halo, alkoxy, or methylcarboxylate group;
R$^3$ is a hydrogen or R$^3$ together with X form a C$_5$ heteroaryl;
R$^4$ and R$^6$ are each independently a hydrogen or phosphonate group; and
R$^5$ is a substituted or unsubstituted aryl or heteroaryl group;
with the proviso that at least one of R$^4$ or R$^6$ is a phosphonate group.

As is conventional in the art, a hydroxyl group is —OH; and a halo group is fluorine, chlorine, bromine or iodine;

As used herein, the term "alkyl" employed alone or in combination with another term includes a straight or branched chain hydrocarbon. If not otherwise defined, alkyl has 1 to 6 carbon atoms. Examples of "C$_{1-5}$ alkyl" are alkyl residues containing 1, 2, 3, 4, 5, or 6 carbon atoms are methyl, ethyl, propyl, butyl, pentyl, or hexyl, the n-isomers of all these residues, isopropyl, isobutyl, 1-methylbutyl, isopentyl, neopentyl, isohexyl, sec-butyl, tert-butyl or tert-pentyl.

The term "alkyoxy" includes an alkyl, as defined herein, bonded to oxygen. Methoxy, ethyoxy, n-propyloxy, isopropyloxy, n-butyloxy, isobutyloxy, sec-butyloxy, tert-butyloxy, n-pentyloxy, isopentyloxy, neo-pentyloxy, n-hexyloxy, iso-hexyloxy, and the like are exemplified as "alkyoxy."

As used herein, the term "aryl" is understood to mean an aromatic hydrocarbon ring containing from 5 to 7 carbon atoms. The term "heteroaryl" means a monocyclic- or polycyclic aromatic ring comprising carbon atoms, hydrogen atoms, and one or more heteroatoms, preferably, 1 to 3 heteroatoms, independently selected from nitrogen, oxygen, and sulfur. As is well known to those skilled in the art, heteroaryl rings have less aromatic character than their all-carbon counter parts. Thus, for the purposes of the invention, a heteroaryl group need only have some degree of aromatic character. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3)- and (1,2,4)-triazolyl, pyrazinyl, pyrimidinyl, tetrazolyl, furyl, thienyl, isoxazolyl, thiazolyl, phenyl, isoxazolyl, and oxazolyl. A heteroaryl group can be unsubstituted or substituted with one or two suitable substituents. Preferably, a heteroaryl group is a monocyclic ring, wherein the ring includes 2 to 5 carbon atoms and 1 to 3 heteroatoms, referred to herein as "C$_{2-5}$ heteroaryl." Exemplary heteroaryls include the following:

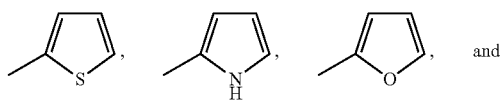

-continued

[Structure: methylpyridine]

If not otherwise defined, alkyl, alkoxy, aryl, and heteroaryl are unsubstituted or mono, di- or tri-substituted independently of one another by groups such as, for example, —F, —Cl, —Br, —I, —CF$_3$, —NO$_2$, —CN, —NH$_2$, —COOH, —OH, —OCH$_3$, —OCF$_3$, —CONH$_2$, -alkyl, -alkoxy or a methylcarboxylate group.

A phosphonate group is understood to mean a —PO(OR$^7$)$_2$ group, wherein each R$^7$ is independently a methyl group or alkyl group as defined herein.

The phrase "R$^3$ together with X forms a C$_5$ heteroaryl," refers to the structure:

[Structure]

In certain embodiments of the invention, R$^1$ is a methoxy group. In other embodiments, R$^1$ is a methylcarboxylate group. In yet other embodiments R$^2$ is a hydroxyl group. In particular embodiments, R$^3$ together with X forms a C$_5$ heteroaryl and X is S. In still other embodiments, R$^4$ is a phosphonate group.

In some embodiments of Formula I, n is 0, and R$^3$ together with X form a C$_5$ heteroaryl. In accordance with this embodiment, the ABAD inhibitor has the structure:

Formula II

[Structure]

wherein
X is S or O;
R$^1$ and R$^2$ are each independently a hydrogen, hydroxyl, halo, alkoxy, or methylcarboxylate group;
R$^4$ is a phosphonate group; and
R$^5$ is a substituted or unsubstituted aryl or heteroaryl group.

Exemplary compounds of Formula II include compounds 4-17. In particular embodiments R$^5$ is a phenol group.

In some embodiments of Formula I, n is 1, Y is C—R$^6$, R$^3$ is hydrogen. In accordance with this embodiment, the ABAD inhibitor has the structure:

Formula III

[Structure]

wherein
X is S or O;
the dashed bonds are independently present or absent;
R$^1$ and R$^2$ are each independently a hydrogen, hydroxyl, halo, alkoxy, or methylcarboxylate group;
R$^4$ and R$^6$ are each independently a hydrogen or phosphonate group; and
R$^5$ is a substituted or unsubstituted aryl or heteroaryl group;
with the proviso that at least one of R$^4$ or R$^6$ is a phosphonate group.

Exemplary compounds of Formula III include compounds 21-26.

The compounds of the invention can be prepared using methods known in the art of organic synthesis. For example, the compounds of the invention, as well as all intermediates, can be synthesized by known processes using either solution or solid phase techniques. Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well-known in the art. For example, numerous protecting groups are described in Greene & Wuts (1991) *Protecting Groups in Organic Synthesis*, Second Edition, Wiley, New York, and references cited therein.

Compounds of the invention can be used as is or prepared as pharmaceutically acceptable salts. As used herein, the term "pharmaceutically acceptable salt" refers to those salts of the compounds of Formula I which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well-known in the art. See, e.g., Berge, et al. (1977) *J. Pharmaceutical Sciences* 66:1-19. Salts can be prepared in situ during the final isolation and purification of the compounds of the invention, or separately by reacting a free base with a suitable organic acid. Examples of pharmaceutically acceptable salts include, but are not limited to, nontoxic acid addition salts formed from amino group and an inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

The term "pharmaceutically acceptable prodrug" as used herein refers to those prodrugs of the inhibitors of Formula I which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug," as used herein refers to a compound which is convertible in vivo by metabolic means (e.g., by hydrolysis) to afford any compound delineated by the formula of the instant invention. Various forms of prodrugs are known in the art, for example, as discussed in Bundgaard (ed.) *Design of Prodrugs*, Elsevier (1985); Widder, et al. (ed.) *Methods in Enzymology*, vol. 4, Academic Press (1985); Krogsgaard-Larsen, et al. (ed.) *Design and Application of Prodrugs, Textbook of Drug Design and Development*, Chapter 5, 113-191 (1991); Bundgaard, et al. (1992) *J. Drug Deliv. Rev.* 8:1-38; Bundgaard (1988) *J. Pharmaceut. Sci.* 77:285; Higuchi & Stella (eds.) *Prodrugs as Novel Drug Delivery Systems*, American Chemical Society (1975).

To demonstrate activity, candidate inhibitors, derivatives, stereoisomers, tautomers, pharmaceutically acceptable salts, or prodrugs thereof, can be tested in vitro for their ability to reduce ABAD activity and/or the Aβ-ABAD interaction. The activity of the inhibitor compounds can be assayed utilizing methods known in the art and/or those methods presented herein. For example, the compounds can be tested for the ability to inhibit the reduction of S-acetoacetyl-CoA (SAAC) and/or in an ELISA-based assay which determines binding between Aβ and ABAD in the presence of the compound. These data can be expressed, for example, as $K_i$, $K_i$ apparent, $V_i/V_o$, or percentage inhibition. $K_i$ is the inhibition equilibrium constant that indicates the ability of compound to inhibit a given enzyme. Numerically lower $K_i$ values indicate a higher affinity of the compounds of the invention for the enzyme. The $K_i$ value is independent of the substrate, and converted from $K_i$ apparent. Compounds demonstrating the ability to cause a detectable decrease ABAD activity can be tested in known cell or animal models of Alzheimer's disease.

For therapeutic and prophylactic applications, one or more inhibitors of the invention can be formulated as a pharmaceutical composition. A pharmaceutical composition contains a therapeutically effective amount of an inhibitor of the present invention formulated together with one or more pharmaceutically acceptable carriers. As used herein, the term "pharmaceutically acceptable carrier" means a nontoxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical composition of this invention may be administered orally, parenterally, by inhalation spray, topically, rectally, nasally, buccally, vaginally or via an implanted reservoir. The pharmaceutical composition of this invention may contain any conventional non-toxic pharmaceutically acceptable carrier, adjuvant or vehicle. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

An inhibitory amount or dose of the compounds of the present invention may range from about 0.1 mg/kg to about 500 mg/kg, alternatively from about 1 to about 50 mg/kg. Inhibitory amounts or doses will also vary depending on route of administration, as well as the possibility of co-usage with other agents.

According to the methods of treatment of the present invention, a subject, such as a human or lower mammal, is administered an effective amount or an inhibitory amount of a compound of the present invention, in such amounts and for such time as is necessary to achieve the desired result. The term "effective amount" of a compound of the invention, as used herein, means a sufficient amount of the compound so as to decrease the signs or symptoms of the disease or disorder in a subject. The actual amount effective for a particular application will depend, inter alia, on the condition being treated. For example, when administered in methods to treat Alzheimer's disease, such compositions will contain an amount of active ingredient effective to achieve the desires result (e.g., decreasing ABAD activity, protecting against aberrant mitochondrial and neuronal function, improving learning memory, and/or reducing mitochondrial and cerebral Aβ accumulation). Determination of a therapeutically effective amount of a compound of the invention is well within the capabilities of those skilled in the art.

It will be understood that the total daily usage of the inhibitors and compositions of the present invention will be decided by the attending physician within the scope of sound medical judgment. The specific therapeutically effective dose level for any particular subject will depend upon a variety of factors including the disorder being treated and the severity of the disorder; the activity of the specific compound employed; the specific composition employed; the age, body weight, general health, sex and diet of the subject; the time of administration, route of administration, and rate of excretion of the specific compound employed; the duration of the treatment; drugs used in combination or contemporaneously with the specific compound employed; and like factors well known in the medical arts.

The total daily dose of the inhibitors of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention include administration to a subject in need of such treatment from about 10 mg to about 1000 mg of the compound(s) of this invention per day in single or multiple doses.

Lower or higher doses than those recited above may be required. Specific dosage and treatment regimens for any particular subject will depend upon a variety of factors, including the activity of the specific compound employed, the age, body weight, general health status, sex, diet, time of administration, rate of excretion, drug combination, the severity and course of the disease, condition or symptoms, the subject's disposition to the disease, condition or symptoms, and the judgment of the treating physician.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

As is well known in the art, therapeutically effective amounts for use in humans can also be determined from animal models. For example, a dose for humans can be formulated to achieve a concentration that has been found to be effective in animals. The dosage in humans can be adjusted by monitoring ABAD inhibition and adjusting the dosage upwards or downwards. Adjusting the dose to achieve maximal efficacy in humans based on animal models and other methods as are well-known in the art is well within the capabilities of the ordinarily skilled artisan.

Having demonstrated inhibitory activity, the ABAD inhibitors of the invention can be employed in methods for decrease, reducing or inhibiting ABAD activity. In accordance with such methods, ABAD is contacted with an effective amount of an inhibitor described herein so that ABAD activity is reduced or inhibited relative to the amount of ABAD activity in the absence of the inhibitor. The ABAD protein can be contacted in any appropriate environment including in vitro, within a cell, or within a mammal. Typically, in vitro solutions are selected such that the components do not substantially interfere with the enzymatic activity of ABAD (e.g., aqueous solutions). In some embodiments, the in vitro solution includes a biological sample, such as a mammalian sample. Exemplary mammalian samples include plasma or serum samples and tissue samples, such as a brain biopsy. Any appropriate cell or cellular sample may be selected in which to contact ABAD with the inhibitor. The cell may contain endogenous ABAD or recombinant ABAD. Exemplary cells include human embryonic kidney (HEK293) cells, HeLa cells, Chinese hamster ovary cells, or neuroblastoma line M17 cells HeLa cells, 293 cells. In an exemplary embodiment, the compounds of the invention are administered to a mammal (e.g., a mouse, rabbit or human) to inhibit ABAD activity.

As described herein, the reduction in activity of an enzyme may be expressed in terms of the inhibitory constant ($K_i$). Where an inhibitor selectively reduces the activity of ABAD, the $K_i$ of the reaction between an inhibitor compound of the invention and ABAD is less than the $K_i$ of the reaction between an inhibitor compound of the invention and any other protein.

In particular embodiments of the present invention, the ABAD inhibitors of the invention are employed in the treatment of diseases or conditions associated with ABAD activity. Typically, a mammal is treated for the disease or condition. In an exemplary embodiment, the disease is Alzheimer's disease. Thus, in certain embodiments, the invention provides a method of ameliorating or treating Alzheimer's disease in a subject (e.g., a human) by of administering to the subject one or more ABAD inhibitors of the invention. The subject treated with the inhibitors may be human primates, nonhuman primates and/or non-human mammals (e.g., rodents, canines).

Amelioration or treatment of Alzheimer's disease in accordance with the instant method refers to halting, reversing or diminishing the progression of the Alzheimer's disease and/or measurably decreasing one or more signs or symptoms of Alzheimer's disease. Moderate Alzheimer's disease signs include memory loss, confusion, problems recognizing people, difficulty with language and thoughts, restlessness, agitation, wandering, and repetitive statements. Severe signs of Alzheimer's disease include weight loss, seizures, skin infections, groaning, moaning, grunting increased sleeping, loss of bladder and bowel control, and complete dependence on others for care.

The invention is described in greater detail by the following non-limiting examples.

Example 1

Materials and Methods

General Procedure to Synthesis of Small Molecular Weight Benzothioazole Phosphonate Derivatives.

To decrease adverse effects, facilitate passage across the BBB, and increase water solubility, phosphonate derivatives were synthesized for use as potential inhibitors for Aβ-ABAD interactions. A series of analogs were synthesized with variations at the aromatic rings and their linking group.

As shown in Table 1, various aromatic/heterocyclic aldehydes (2) were individually mixed with $Mg(ClO_4)_2$ (5 mol %) in anhydrous toluene (5 mL). The mixture was stirred magnetically for 10-15 minutes, after which time substituted benzothiazole amines (1) and dimethyl/diethyl phosphite (3) in anhydrous toluene (5 mL) were added drop-wise with stirring at room temperature for 30 minutes. The reaction mixture was refluxed with stirring for 5-12 hours. After completion of the reaction, as determined by TLC (ethyl acetate:hexane), the solvent was removed in a rotary-evaporator. The reaction mixture was extracted with EtOAc (3×10 mL). The combined EtOAc extracts were dried ($Na_2SO_4$) and concentrated under reduced pressure to afford products 4-17, which were passed through a column of silica gel and eluted with EtOAc-hexane.

TABLE 1

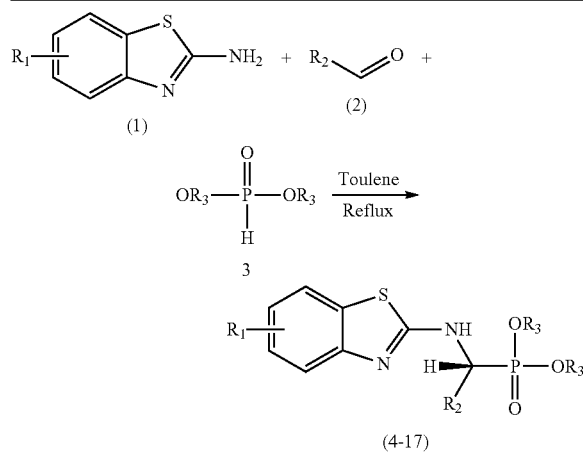

| Compound | $R_1$ | $R_2$—CHO | $R_3$ |
|---|---|---|---|
| 4 | OMe | 5-COOCH$_3$, 4-OH•C$_6$H$_3$ | Methyl |
| 5 | F | 5-COOCH$_3$, 4-OH•C$_6$H$_3$ | Methyl |
| 6 | OMe | 5-COOCH$_3$, 4-OH•C$_6$H$_3$ | Ethyl |
| 7 | OMe | 5-COOCH$_3$, 4-OH•C$_6$H$_3$ | Ethyl |
| 8 | OMe | 4-OH•C$_6$H$_4$ | Methyl |
| 9 | OMe | 2-OH•C$_6$H$_4$ | Methyl |
| 10 | OMe | 2-S•C$_4$H$_3$ | Methyl |
| 11 | OMe | 2-NH•C$_4$H$_3$ | Methyl |
| 12 | OMe | 4-F•C$_6$H$_4$ | Ethyl |
| 13 | OMe | 2-O•C$_4$H$_3$ | Methyl |
| 14 | OMe | 4-OH•C$_6$H$_4$ | Ethyl |
| 15 | OMe | 4-F•C$_6$H$_4$ | Methyl |
| 16 | OMe | 4-F•C$_6$H$_4$ | Ethyl |
| 17 | OMe | 5-Br, 2-OH•C$_6$H$_4$ | Ethyl |

Mg(ClO$_4$)$_2$ was found to be an extremely efficient catalyst for the formation of benzothiazole amino phosphonates by a one pot, three-component reaction of an aromatic/heterocyclic aldehydes, substituted benzothiazole amines, and a dimethyl/diethyl phosphite in dry toluene (Table 1).

General Procedure for Synthesizing Urea Phosphonate Derivatives (Table 2).

A mixture of urea/thiourea (1 mmol) and methyl 5-formyl-2-hydroxybenzoate (2 mmol) in ethanol (15 mL) was refluxed for the appropriate reaction (TLC) time. The solvent was evaporated in vacuo and the resulting crude material was purified by chromatography on a short column of silica gel (EtOAc: petroleum ether, 1:3) and then recrystallized from ethanol/dichloromethane (4:1) to afford the urea derivatives.

A mixture of urea derivatives (1 mmol), toluene (20 mL), and dimethyl phosphite (DMP)/diethyl phosphate (DEP) (2 mmol) was heated at 110° C. for 15 hours. The solvent was evaporated in vacuo and the resulting crude material was purified by chromatography on a short column of silica gel (EtOAc: dichloromethane, 1:3) and then recrystallized from ethanol (4:1) to afford the target molecules.

TABLE 2

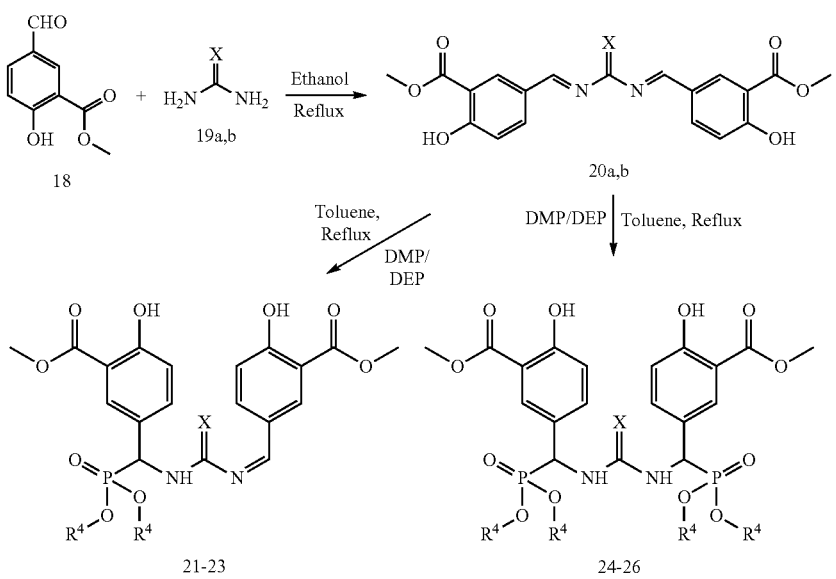

| Compound | X | R |
|---|---|---|
| 21 | S | Methyl |
| 22 | O | Methyl |
| 23 | S | Ethyl |
| 24 | O | Ethyl |
| 25 | S | Methyl |
| 26 | O | Ethyl |

Spectral Data of Selected Compounds. Melting points were determined in open capillary tubes on a Laboratory Devices Mel-Temp apparatus and were uncorrected. $^{1}$H and $^{13}$C NMR spectra were recorded in $d_6$-DMSO on a Bruker DRX-500 spectrometer operating at 500 MHz, and 125 MHz, respectively and calibrated to the solvent peak. $^{31}$P NMR spectra was recorded on Bruker DRX-400 spectrometer operating at 162 MHz. High-resolution mass spectrometry (HRMS) was recorded on a LCT Premier Spectrometer (Micromass UK Limited) operating on ESI (MeOH).

Methyl 5-((dimethoxyphosphoryl)((6-methoxybenzo[d]thiazol-2-yl)amino)methyl)-2-hydroxybenzoate (4). The mixture of methyl 5-formyl-2-hydroxybenzoate (2) (0.1 g, 5 mmol) and Mg(ClO$_4$)$_2$ (0.12 g, 5 mol %) was stirred for 10-15 minutes in anhydrous toluene (5 mL), after which time 6-methoxybenzo[d]thiazol-2-amine (1) (0.1 g, 5 mmol) and dimethyl phosphite (0.061 g, 5 mmol) were added, and the reaction mixture was refluxed for 6 hours. The progress of the reaction was monitored by TLC (Dichloromethane:EtOAc=1:9). After completion of the reaction, the solvent was removed under reduced pressure. The combined EtOAc extracts were dried (Na$_2$SO$_4$) and concentrated under reduced pressure to afford a white solid, which was purified by passing through silica gel column using EtOAc: dichloromethane (4:1) as eluent to afford compound (4). The same experimental procedure was adopted for the preparation of the remaining title compounds 5-7, 9-14 and 16-17.

Methyl 5-((dimethoxyphosphoryl)((6-methoxybenzo[d]thiazol-2-yl)amino)methyl)-2-hydroxybenzoate (4). $R_f$=0.26 (1:9 Hexane/EtOAc); mp: 215-216° C.; FTIR (thin film): 3161, 3114, 3002, 2952, 2842, 1677, 1604, 1217 cm$^{-1}$; $^{1}$H NMR (500 MHz, d6-DMSO) (ppm) 10.48 (s, 1H), 7.91-7.90 (m, 1H), 7.66-7.64 (m, 1H), 7.23-7.22 (m, 1H), 7.06 (d, J=10.0 Hz, 1H), 6.95 (d, J=10.0 Hz, 1H), 6.89-6.87 (m, 2H), 4.32 (d, J=15.0 Hz, 1H), 3.90 (s, 3H), 3.72 (s, 3H), 3.55 (d, J=10.0 Hz, 3H), 3.44 (d, J=10.0 Hz, 3H). $^{13}$C NMR (125 MHz, d$_6$-DMSO) (ppm) 169.2, 159.10 (d, J=2.5 Hz), 157.5, 154.4, 135.7 (d, J=5.0 Hz), 134.4, 129.4, 129.2 (d, $J_{CP}$=6.25 Hz), 122.2, 116.8, 112.6, 112.2 (d, J=2.5 Hz), 109.9, 108.1, 66.7, 65.4, 55.6, 52.9 (d, $J_{CP}$=7.5 Hz), 52.4. $^{31}$P NMR (162 MHz, d6-DMSO) (ppm) 18.39; HRMS calcd for C$_{19}$H$_{22}$N$_2$O$_7$PS (M+H)$^{+}$ 453.0885. found 453.0883 (TOF MS ES$^{+}$).

Methyl 5-((dimethoxyphosphoryl)((6-fluorobenzo[d]thiazol-2-yl)amino)methyl)-2-hydroxybenzoate (5). Rf=0.3 (1:2 MeOH/EtOAc); M.P: 258-259° C.; FTIR (thin film): 3310, 3211, 3055, 2985, 2954, 1679, 1606, 1265 cm$^{-1}$; $^{1}$H NMR (500 MHz, d$_6$-DMSO) δ (ppm) 10.41 (s, 1H), 8.65 (s, 1H), 7.85 (s, 1H), 7.61 (m, 1H), 7.48 (m, 1H), 7.24 (m, 1H), 6.99-6.93 (m, 1H), 6.88 (d, J=15.0 Hz, 1H), 4.90 (d, J=20.0 Hz, 1H), 3.85 (s, 3H), 3.33 (s, 6H); $^{13}$C NMR (125 MHz, d$_6$-DMSO) (ppm) 169.5, 166.2, 158.7, 157.8, 155.9, 148.9, 135.8, 131.8, 128.5, 118.0, 116.3, 112.4, 111.7, 107.6, 56.4, 55.3, 52.2, 51.6, 48.5; $^{31}$P NMR (162 MHz, d$_6$-DMSO) δ (ppm) 12.55; HRMS calcd for C$_{18}$H$_{18}$FN$_2$O$_6$PS (M−H) 439.0529. found 439.0551 (TOF MS ES−).

Methyl 5-((diethoxyphosphoryl)((6-methoxybenzo[d]thiazol-2-yl)amino)methyl)-2-hydroxybenzoate (6). Rf=0. (1:5 MeOH/EtOAc); M.P: 241-243° C.; FTIR (thin film): 3310, 3128, 3010, 2986, 2952, 1668, 1607, 1221 cm-1; $^{1}$H NMR (500 MHz, d$_6$-DMSO) δ (ppm) 10.47 (s, 1H), 8.73 (s, 1H), 77.92-7.89 (m, 1H), 7.64-7.61 (m, 1H), 7.32-7.22 (m, 2H), 7.02-6.92 (m, 1H), 6.83-6.77 (m, 1H), 5.55 (dd, J=20.0, 20.0 Hz, 1H), 3.90-4.01 (m, 4H), 3.89 (s, 3H), 3.73 (s, 3H), 1.08 (t, 6H); $^{13}$C NMR (125 MHz, d$_6$-DMSO) δ (ppm) 169.2, 169.1, 159.1, 154.3, 145.6, 135.5, 131.7, 129.1, 118.4, 116.9, 112.9, 112.7, 112.4, 105.4, 61.5, 55.4, 52.4, 16.3; $^{31}$P NMR (162 MHz, d$_6$-DMSO) δ (ppm) 21.50; HRMS calcd for C$_{21}$H$_{25}$N$_2$O$_7$PS (M+H)+ 481.1191. found 481.1198 (TOF MS ES+).

Dimethyl ((4-hydroxyphenyl)((6-methoxybenzo[d]thiazol-2-yl)amino)methyl)phosphonate (8). The mixture of 4-hydroxybenzaldehyde (2) (0.067 g, 5 mmol) and Mg(ClO$_4$)$_2$ (0.12 g, 5 mol %) was stirred for 10-15 minutes in anhydrous toluene (5 mL), after which time 6-methoxybenzo[d]thiazol-2-amine (1) (0.1 g, 5 mmol) and diethyl phosphite (0.076 g, 5 mmol) were added, and the reaction mixture was refluxed for 3 hours followed by usual workup and chromatographic purification [silica gel: EtOAc-Dichloromethane (8.5:1.5) as eluent] afforded the dimethyl ((4-hydroxyphenyl)((6-methoxybenzo[d]thiazol-2-yl)amino) methyl)phosphonate as colorless solid.

$R_f$=0.2 (8.5:1.5 EtOAc-Dichloromethane); mp: 178-180° C.; FTIR (thin film): 3200, 2985, 2958, 1602, 1265 cm-1; $^{1}$H NMR (500 MHz, d$_6$-DMSO) (ppm) 9.48 (s, 1H), 8.77-8.73 (m, 1H), 7.32-7.30 (m, 4H), 6.84-6.81 (m, 1H), 6.76-6.74 (m, 3H), 5.56 (dd, J=10.0, 10.0 Hz, 1H), 3.73 (s, 3H), 3.65 (d, J=10.0 Hz, 3H), 3.50 (d, J=10.0 Hz, 3H). $^{13}$C NMR (125 MHz, d$_6$-DMSO) (ppm) 163.7 (d, J=10.0 Hz), 157.0 (d, J=2.5 Hz), 154.5, 145.6, 131.8, 129.3 (d, J=5.0 Hz), 125.7, 118.6, 115.0, 112.9, 105.5, 99.5, 55.5, 53.8, 53.2 (d, $J_{CP}$=7.25 Hz), 52.6. $^{31}$P NMR (162 MHz, d$_6$-DMSO) (ppm) 23.81; HRMS calcd for C$_{17}$H$_{19}$N$_2$O$_5$PS (M+H) 395.0831. found 395.0824 (TOF MS ES$^{+}$).

Dimethyl (((6-methoxybenzo[d]thiazol-2-yl) amino)(thiophen-2-yl) methyl) phosphonate (10). Rf=0.32 (1:5 CH$_2$Cl$_2$/EtOAc); Melting Point: 189-190° C.; FTIR (thin film): 3382, 2983, 2929, 1602, 1191 cm-1; $^{1}$H NMR (500 MHz, d$_6$-DMSO) δ (ppm) 8.77 (s, 1H), 7.45 (d, J=5.0, 1H), 7.33-7.31 (m, 2H), 7.20-7.19 (m, 1H), 7.02-6.99 (m, 1H), 6.88-6.81 (m, 1H), 5.76 (dd, J=20.0, 1H), 3.74 (s, 3H), 3.58 (d, J=10.0, 6H); $^{13}$C NMR (125 MHz, d$_6$-DMSO) δ (ppm) 163.8.5 (d, JCP=8.7 Hz), 154.5 (d, JCP=13.7 Hz), 145.3, 139.4, 126.7, 126.2, 125.3, 118.5, 112.9, 105.5, 59.7, 55.8, 52.7.

$^{31}$P NMR (162 MHz, d$_6$-DMSO) δ (ppm) 17.73; HRMS: calcd for C$_{15}$H$_8$N$_2$O$_4$PS$_2$ (M+H)+ 385.0446. found 385.0435 (TOF MS ES+).

Dimethyl (((6-methoxybenzo[d]thiazol-2-yl)amino) (1H-pyrrol-2-yl)methyl)phosphonate (12). Rf=0.25 (5:95 EtOAc/CH$_2$Cl$_2$); M.P: 191-192° C.; FTIR (thin film): 3305, 3210, 3053, 2987, 2929, 1606, 1217 cm-1; $^{1}$H NMR (500 MHz, d$_6$-DMSO) (ppm) 8.66 (s, 1H), 7.45 (d, J=10, 1H), 7.33-7.22 (m, 3H), 6.83-6.75 (m, 2H), 6.09 (s, 1H), 5.76 (dd, J=20.0, 20.0 Hz, 1H), 3.73 (s, 3H), 3.52 (d, J=10.0, 6H); $^{13}$C NMR (125 MHz, d$_5$-DMSO) δ (ppm) 164.2, 154.4, 145.2, 131.4, 130.8, 127.5, 118.3, 117.6, 112.9, 110.1, 105.5, 55.4, 52.5, 50.2; $^{31}$P NMR (162 MHz, d$_6$-DMSO) δ (ppm) 17.52; HRMS: calcd for C$_{15}$H$_{18}$N$_3$O$_4$PS (M+H)+ 368.0728. found 368.0732 (TOF MS ES+).

Diethyl ((4-hydroxyphenyl) ((6-methoxybenzo[d]thiazol-2-yl)amino)methyl)phosphonate (14). Rf=0.2 (1:5 MeOH/EtOAc); M.P: 178-180° C.; FTIR (thin film): 3200, 2985, 2958, 1602, 1265 cm-1; $^{1}$H NMR (500 MHz, d$_6$-DMSO) δ (ppm) 8.68 (s, 1H), 7.49-7.45 (m, 1H), 7.32-7.27 (m, 2H), 7.13-7.07 (m, 1H), 6.84-6.79 (m, 3H), 5.90 (dd, J=20.0, 20.0 Hz, 1H), 4.04-3.90 (m, 5H), 3.73 (s, 3H), 1.02-1.08 (m, 6H); $^{13}$C NMR (125 MHz, d$_6$-DMSO) δ (ppm) 164.2, 163.8, 154.6, 145.6, 144.9, 128.7, 123.8, 118.1, 115.4, 112.9, 105.4, 62.2, 60.1, 55.4, 16.2; $^{31}$P NMR (162 MHz, d$_6$-DMSO) δ (ppm) −1.77, 1.47, 4.68; HRMS cadd for C$_{19}$H$_{23}$N$_2$O$_5$PS (M+H)+ 323.212. found 323.216 (TOF MS ES+).

Dimethyl ((4-fluorophenyl) ((6-methoxybenzo[d]thiazol-2-yl) amino) methyl) phosphonate (15). The mixture of methyl 4-fluorobenzaldehyde (2) (0.068 g, 5 mmol) and Mg(ClO$_4$)$_2$ (0.12 g, 5 mol %) was stirred for 10-15 minutes in anhydrous toluene (5 mL), after which time 6-methoxybenzo[d]thiazol-2-amine (1) (0.1 g, 5 mmol) and dimethyl phosphite (0.061 g, 5 mmol) were added, and the reaction mixture was refluxed for 1.3 hours followed by usual workup and chromatographic purification [silica gel: EtOAc-CH$_2$Cl$_2$ (1:5) as eluent] afforded the dimethyl ((4-fluorophenyl) ((6-methox benzo[d]thiazol-2-yl) amino) methyl) phosphonate as colorless solid:

R$_f$=0.3 (1:5 CH$_2$Cl$_2$/EtOAc); mp: 178-180° C.; FTIR (thin film): 3214, 3053, 2985, 2927, 1298, 1265 cm-1; $^1$H NMR (500 MHz, d$_6$-DMSO) (ppm) 8.78 (s, 1H), 7.53-7.44 (m, 2H), 7.30-7.22 (m, 2H), 7.18-7.12 (m, 2H), 6.82-6.77 (m, 1H), 5.46 (d, J=20.0 Hz, 1H), 3.72 (s, 3H), 3.50 (d, J=10.0 Hz, 6H). $^{13}$C NMR (125 MHz, d$_6$-DMSO) (ppm) 164.1 (d, J=10.0 Hz), 162.2, 160.3 (d, J=15.0 Hz), 154.3, 145.7, 131.8, 129.8, 118.4, 114.8 (d, J=21.25 Hz), 112.8, 105.4, 55.4, 55.1, 53.9, 52.3 (d, J$_{CP}$=6.25 Hz). $^{31}$P NMR (162 MHz, d$_6$-DMSO) (ppm) 16.96; HRMS cald for C$_{17}$H$_{20}$FN$_2$O$_4$PS (M+H) 397.0787. found 397.0795 (TOF MS ES$^+$).

Diethyl ((4-fluorophenyl)((6-methoxybenzo[d]thiazol-2-yl)amino)methyl)phosphonate (16). Rf=0.37 (1:3 MeOH/EtOAc); M.P: 198-200° C.; FTIR (thin film): 3332, 3053, 2950, 2840, 1610, 1265 cm-1; $^1$H NMR (500 MHz, CDCl$_3$) δ (ppm) 8.86 (s, 1H), 7.60-7.56 (m, 2H), 7.46 (d, J=10.0 Hz, 1H), 7.12-7.03 (m, 3H), 6.93-6.88 (m, 1H), 5.50 (d, J=30.0 Hz, 1H), 4.28-3.99 (m, 5H), 3.81 (s, 3H), 1.09 (t, 6H); $^{13}$C NMR (125 MHz, CDCl3) δ (ppm) 163.93 (d, JCP=40.0 Hz), 161.6, 155.5, 130.9, 129.9, 129.8, 119.6, 115.6, 115.4, 113.5, 105.3, 63.6, 55.8, 54.5, 16.4; $^{31}$P NMR (162 MHz, CDCl$_3$) δ (ppm) 21.18; HRMS cald for C$_{19}$H$_{22}$FN$_2$O$_4$PS (M+H)+ 425.1100. found 425.1100 (TOF MS ES+).

Lead Optimization.

The following steps were carried out for lead optimization. Starting with group of 20 benzothiazole phosphonates, QSAR descriptors with Lipinski rules were used to determine ADME properties. These descriptors were standardized using known drug-like molecules. Principal Component Analysis (PCA) is used to determine if a proposed molecule is clustered in a drug-like region of component space. An alternative approach is to use commercially available integrated software as a drug-like filter. For example, eADMET, GmbH provides software for the prediction of important properties of chemicals and drugs, especially physical and ("drug-like") characteristics. The software develops computational models designed to predict the ADMET (absorption, distribution, metabolism, excretion and toxicity) of molecules.

When enough activity data was collected, drug candidates were assessed for potential activity. This QSAR filter was generated by defining descriptors that best fit the measured activity range of the generated ligands. A QSAR plot of observed activity versus predicted activity, based on defined descriptors, was constructed by linear regression methods. The accuracy of the descriptors was usually reflected by a correlation factor (R$^2$). An activity estimate of the unknown candidates was assessed by correlating their calculated value to the observed estimate. This QSAR approach becomes valuable when dealing with large quantities of drug candidates, such as virtual libraries generated by combinatorial methods.

Another approach to assess activity using the MOE software is 3D pharmacophore modeling. As certain regions of the ABAD active site appear to be import for ligand binding these volumes can be defined in terms of size and interaction type (H-bond acceptor or donor, hydrophobic, etc.). This 3D filter was used in conjunction with QSAR methods to evaluate large virtual libraries for potential activity and synthesis.

Ligand site identification was subsequently identified by crystal structures of ABAD ligand complexes. The observed crystal binding site was consistent and supported by the MOE Alpha Site Finder algorithm. Ligand docking was carried out and each candidate was ranked by a scoring functions: London DG free energy and interaction energy, DE. Molecular candidates above a defined scoring threshold were selected for synthesis. In vitro screens were used to measure Aβ-ABAD inhibition. The lead candidate was determined as having the highest activity. It was replaced if another candidate was observed to have higher activity. All candidates that passed the threshold criteria were slotted to be structural templates for improved candidates by modification. All candidates that failed the threshold criteria were eliminated.

Ligand candidate modification was carried out in MOE's LigX module, where an active candidate can be modified either by changing functional groups or scaffold (nucleus). The binding energy was readily calculated, and the modification was accepted as a potentially more active ligand candidate if binding energy was below a defined threshold. At this point, virtual libraries could be constructed if a ligand demonstrates that a certain surface region is important for binding to the receptor protein. The cycle is reiterated until an acceptable lead candidate activity is achieved, i.e., low nM to pM region. Importantly, MOE is setup to operate at each of these steps in high throughput mode.

Construction of Models and Molecular Dynamics of the Novel Leads.

The 3D structure of all ligands were constructed in MOE (Molecular Operating Environment) working environment and subjected to energy minimization (Caspersen, et al. (2005) supra; Lin & Beal (2006) supra; Vilar, et al. (2008) Curr. Top. Med. Chem. 8:1555). An MMFF94x force field was included and the related potential energy terms were enabled for all bonded interactions, van der Waals interactions, electrostatic interactions and restraints. The non-bonded cut off value was enabled between 8-10 Ang. Generalized Born implicit salvation model was enabled and all the parameters were fixed. The gradient was set to 0.05 and force filed partial charges were enabled to calculate during minimization process. The dynamics simulations were carried out in Nose-poincare Anderson equational algorithm. The temperature was set to 30K and increased to 300K run time temperature. Heat time and cool time were set to 0 picoseconds. The final stabilized conformations were used for the construction of a local data base of present novel leads and chosen to determine 2D and 3D descriptors, including Lipinski rules that define drug-like properties.

3D Quantitative Structure-Activity Relationship (QSAR) and Comparative Molecular Field Analysis.

The QSAR suite of applications in MOE was used to calculate and analyze the data and build numerical models of the data for prediction and interpretation purposes. Any QSAR model for a given set of molecules correlates the activities with properties inherent to each molecule in the set itself. Databases were constructed for five known compounds (Marques, et al. (2009) supra; Xie, et al. (2006) supra) and 20 test compounds, which were considered as training and test data sets, respectively. The descriptors like molar refractivity, SlogP, Density, polar surface area are important in describing such systems. Initially, the QSAR descriptors SlogP, Density, Molar refractivity, Molecular weight, atomic polarizability, log P(o/w), log S, Polar surface area, Van der Waals volume and radius of gyration were calculated for the five training set of molecules.

Fitting the Experimental Data.

SlogP was chosen as dependent variable and the remaining descriptors as independent variables of the database. QSAR model was constructed choosing SlogP as activity field and the remaining descriptors as model fields. Regression analysis was performed for the training data set and Root Mean Square Error (RMSE) and $r^2$ values of the fit were reported. This fit model was saved and used for the prediction of activities of compounds of test data set.

Cross-Validating the Model.

The above QSAR fit was used for both model validation and cross validation. This validation procedure evaluates the predicted activities and the residuals for the training set molecules. The predicted, residual and Z-score values were calculated for both model and cross validations.

Graphical Analysis.

This analysis was used to identify outliers of the fit that had Z-scores beyond the range. The predictive ability of the model was assessed using a correlation plot by plotting the SlogP values (X-axis) versus the predicted activities (Y-axis).

Estimation of Predicted Activities of Test Set.

The QSAR model fit obtained above was used to evaluate the predicted SlogP values of 20 test set compounds. The residuals between the SlogP values for the entries in the test set and the predicted values were calculated using the Molecular Database Calculator.

Pruning the Descriptors.

Pruning the descriptors is necessary to select the optimum set of molecules under consideration. 'QuaSAR-Contingency', a statistical application in MOE was used to describe the best molecules in the data set. The results were analyzed using Principle Component Analysis (PCA) and the purpose of which is to reduce the dimensionality of set of molecular descriptors by linearly transforming the data. A report was generated by considering the component limit as zero and minimum variance of 98. Three-dimensional scatter graphical plot was generated using the first three Principal Components (PCA1, PCA2 and PCA3).

Absorption, Distribution, Metabolism, Excretion, & Toxicity (ADMET) Prediction.

ADMET properties of the 20 novel compounds were calculated using the preADMET online server. The ADMET properties, human intestinal absorption, in vitro Caco-2 cell permeability, in vitro Maden Darby Canine Kidney (MDCK) cell permeability, in vitro plasma protein binding and in vivo blood brain barrier penetration were predicted using this program.

Preparation of ABAD Protein.

The three-dimensional structure of ABAD was retrieved from Protein Data Bank (PDB ID: 1SO8). To relieve any close contacts, the protein structure was loaded into MOE molecular modeling software and all the water molecules and hetero atoms were removed and polar hydrogen's were added. Protonation of 3D structure was carried out for all the atoms in implicit solvated environment at the specified temperature of 300K, pH of 7 and with a salt concentration value of 0.1. Electrostatic potential was applied to a cut off value of 1.5 Å at a dielectric value of 1. A non-bonded cut off value of 8 Å was applied to the Leonard-Jones terms. After the protonation, the complete structure was Energy minimized in MMFF94x force field at a gradient cut off value of 0.05. Molecular dynamics simulations were carried out at a constant temperature of 300 deg K for a heat time of 10 picoseconds. The total simulations were carried out for a total period of 10 nanoseconds. The time step was considered as 0.001 and the temperature relaxation time was set to 0.2 picoseconds. The position, velocity and acceleration were saved per every 0.5 picoseconds.

Prediction of Binding Site for Ligands.

The binding site for ABAD was predicted through PDBSum. The protein structural information was analyzed at PDBSum and its link to Catalytic Site Atlas (CAS) was followed. The catalytic site residues were Asn121, Ser155, Tyr168 and Lys172, which were based on the structure of Trihydroxynaphthalene Reductase (1YBV).

Molecular Docking.

The ligand database generated from the list of all novel ligand molecules was docked into the specified binding domain of the ABAD receptor. A total of 30 conformations were generated for each Ligand-Receptor complex and among them, the conformation with least docking score was considered for further analysis. The interaction of all ligand molecules in the binding domain cavity was analyzed from ligand interaction study of MOE. The ligand-receptor complexes were analyzed by both London $\Delta G$ free energy approximations and interaction energies, $\Delta E$.

Assay of ABAD Enzymatic Activity.

The assay for the inhibition of reduction of S-acetoacetyl-CoA (SAAC) by ABAD was carried out with ABAD (418 ng/ml), SAAC (172 μM), NADH (102 μM), and different concentrations of inhibitors (from 0 to 1000 μM) in 93 mM potassium phosphate buffer (pH 7.3). Before the assay, all the assay components except SAAC were pre-incubated for 5 minutes, and the reaction started with the addition of SAAC into the reaction mix. The reaction was carried out for a total 6 minutes at room temperature under steady-state conditions, and the decrease of NADH absorbance at 340 nm was determined every 10 seconds. Kinetic data were analyzed by PRISM (Scitech, San Diego, Calif.) to determine $IC_{50}$ values and $K_i$. One unit of enzyme activity was defined as that which converted 1.0 μmol of substrate to product per minute.

Isolation of Brain Mitochondria.

Brain from mice without white matter was used for mitochondrial isolation. Brain was homogenized in 9 ml of ice-cold EB buffer (1 mmol EDTA, 1-6 mg/ml BSA) using a Dounce homogenizer until no particles could be seen. Homogenates were centrifuged at 1300×g for 5 minutes. Supernatant from this fraction was carefully laid on top of a 15% PERCOLL solution (10 ml) and then centrifuged at 16000 RPM for 10 minutes. The pellet was carefully mixed with 9 ml of mitochondrial buffer (4.098% D-mannitol, 2.56% sucrose, 0.034% $K_2HPO_4$, pH 7.3-7.4) and 200 μl of 1% digitonin. After 5 minutes incubation on ice, the mixture was centrifuged at 8000 RPM for 10 minutes. Mitochondrial pellet was washed once with mitochondrial buffer. Subsequently, the mitochondrial pellet was resuspended in 100 μl of mitochondrial buffer and was used for further experiments.

Mitochondria Swelling Assay.

A proper amount of mitochondria was resuspended into 1 ml swelling assay buffer (150 mM KCl, 2 mM $KH_2PO_4$, 10 mM HEPES, pH 7.4) and energized by 1 mM glutamate and 1 mM malate. Calcium at varying concentrations was added into the assay buffer to trigger mitochondrial swelling. Mitochondrial permeability transition was determined by studying the rate of change in absorbance at 540 nm via a spectrophotometer.

Binding Experiment with ABAD.

The interactions between compounds and ABAD were performed using the dual flow cell BIACORE 3000 instrument. Surface Plasmon Resonance (SPR) studies were performed on a BIACORE 3000 at 25° C. SPR binding experiments with ABAD were performed in phosphate-buffered saline (PBS, pH 7.4, 0.005% surfactant P20) as the running and the sample buffer. The surface of the sensor chip was first activated with mixtures of N-hydroxysuccinimide (NHS, 115 mg/ml) and N-(3-dimethyl-aminopropyl)-N'-ethyl-carbodiimide-hydrochloride (EDC, 750 mg/ml) for 7 minutes. ABAD was dissolved in PBS buffer (pH 5.0) at a concentration of 10 µg/ml. The protein was immobilized directly and covalently on the hydrophilic carboxymethylated dextran matrix of the CM5 sensor chip (BIACORE) by using the standard primary amine coupling reaction on a CM5 sensor chip according to standard procedures. After the immobilization of the protein, excess activated carboxylic acid groups were quenched with ethanolamine (1 M, pH 8.5).

Special care was taken during injection of samples because of carryover effects. Special washing routines were used to clean the system before injection of new samples. In addition, predipping of needles was performed. The sample flow was 40 µl/minute in experiments performed for the determination of the kinetic and equilibrium constants. Regeneration of the surfaces between subsequent binding experiments was achieved by washing the surface extensively (>>1 hour) with buffer solution. Data analyses were carried out using BIA evaluation software, and the sensorgrams were processed by automatic correction for nonspecific bulk refractive index effects. The kinetic analyses of the ligand binding to the protein were performed based on the 1:1 Langmuir binding fit model according to the standard procedures described in the software manual.

Immunoprecipitation and Immunoblot Analysis for Detection of Aβ-ABAD Complex.

Mitochondria from cerebral cortices of transgenic mice or human subjects were resuspended in buffer (500 mg/ml, 50 mM Tris, 150 mM NaCl, 1 mM EDTA, protease inhibitors (Calbiochem, set V, EDTA-free), 0.1% NP-40, pH 7.5) and subjected to five freeze-thaw cycles, followed by centrifugation at 14,000 g for 5 minutes at 41° C. The resulting supernatant was immunoprecipitated with mouse antibody to ABAD (1:500 dilution) at 4° C. overnight, followed by a second incubation with protein A/G (Pierce) for 2 hours at 20° C. The resultant immunoprecipitant was subjected to immunoblot analysis with antibody to Aβ (6E10, 1:3,000, Signat).

ELISA Protocol.

96-well plates were coated with commercially available 41-42 and then blocked with 2% of BSA (150 µL per well). After washing, different amounts of biotin-labeled recombinant ABAD were added followed by incubation at 37° C. for 2.5-3.0 hours. The amount of ABAD bound to the plates was detected using EXTRAVIDIN-Peroxidase (Sigma) according to the manufacturer's protocol. For measuring the inhibitory activity, the testing agents were added to the plates before addition of biotin-labeled ABAD.

Method of Measurement of Mitochondrial Cytochrome c Oxidase (CcO) Activity.

The CcO activity was measured according to known methods (Du, et al. (2008) *Nat. Med.* 14:1097-105) with a cytochrome c oxidase kit (Sigma). In brief, SK-N-SH cells were incubated with ABAD inhibitor and oligomer Aβ for 48 hours. After washing the cells twice with PBS, the cells were collected and concentration was determined by the Bradford method. A suitable volume of cells and enzyme solution was added to 475 µl assay buffer. The reaction was triggered by the addition of 25 µl freshly prepared ferrocytochrome C substrate solution into the cuvette. Changes in OD550 nm were recorded immediately with an Amersham Biosciences ULTROSPECT 3100 pro spectrophotometer. The kinetic program had a 5 s delay, 10 s interval; a total of six readings.

Cell Survival and Toxicity Assay.

The MTT (3-(4,5-dimethylthiazol-2-yl)-2,5-diphenyltetrazolium bromide) assay, which is widely used to measure cell proliferation and to screen for anticancer drugs, was used for assessing cell viability. Cells were treated with a range of ABAD compounds at 1, 10, 50, and 100 µM for 48 hours and then subjected to MTT reduction assay following the manufacture's instruction.

The trypan blue dye exclusion is commonly used for measuring cell viability and toxicity. 48-66 hours after treatment of ABAD compounds, the trypan blue exclusion experiments were performed. In brief, cells plated in 96-well plates were washed with the balanced salt solution (Hanks-Balanced Salts/HBSS) once, then replaced with HBSS including trypan blue solution to the final concentration of 0.2% (Sigma-Aldrich, St. Louis, Mo.), and mixed thoroughly. After standing at room temperature for 5 minutes, the cells were washed with HESS again and then maintained in the well with HBSS. Both the stained and unstained cells in each well were counted under a microscope (Nikon E400). The calculated percentage of unstained cells represented the percentage of viable cells. Cell viability (%)=total viable cells (unstained)/total cells (stained and unstained)×100.

Statistical Analysis. Statistical analyses were performed with one-way analysis of variance (ANOVA) using the Statview statistics software (SAS Institute, Version 5.0.1) with Bonferroni/Dumn posthoc test. P<0.05 was considered significant. All data are expressed as means±s.e.m.

Liquid chromatography (LC) Method for mass spectrometry (MS) Detection.

Chromatographic separation was on an ACE C18 column (Mac Mod Analytical, 3 µm, Ultra-Inert HPLC Column, 50×2.1 mm) protected by a matched ACE guard cartridge. Separation solvents were A: $H_2O$ (99%), methanol (1%), and formic acid (0.1%) and B: $H_2O$ (1%), methanol (99%), and formic acid (0.1%) delivered at a flow rate of 400 µl/minute. The hydrophobic character of the analytes allows a large injection (50 µl) to chromatofocus on a column at 5% B. After 0.2 minutes separation was with a linear gradient of 11% B/minute for 4 minutes. Column wash was to 80% B for 2 minutes and re-equilibration at 5% B for 1.5 minutes for a total run-time of 8 minutes. The first 2 minutes of chromatographic effluent was diverted to waste.

Mass Spectrometry Parameters. The mass spectrometer was run in positive ion mode using the electrospray ionization (ESI) source. The source block was 100° C. and desolvation gas temperature 300° C. Argon collision gas pressure on a line to the cell was 1E-3 mbar. Quadrupoles 1 and 3 were set to 0.9 amu FWHH and collision energy and cone voltage settings were optimized for each compound. The data were processed using MassLynx 4.1/QuanLynx and Graphpad Prism 5. Fragmentation patterns of compounds 4, 8, and 15, methyl (Z)-3-(((6-methoxybenzo[d]thiazol-2-yl)imino)methyl)benzoate, 4-(1-((6-methoxybenzo-[d]thiazol-2-yl)amino)ethyl)phenol, and (Z)-1-(4-fluorophenyl)-N-(6-methoxybenzo[d]thiazol-2-yl) methanimine were determined by infusing an aqueous/methanol solution introduce with a T fitting into 30% solvent B from the UPLC for source optimization. The most abundant transitions were chosen for all the three compounds.

Preparation of Calibration Standards for Recovery and Quality Controls.

Stock solutions of 4, 8, and 15 and internal standards (IS) of 1 mM in methanol were used to create calibration standards. Fifty microliters of IS (1 µg/ml) plus 50 µl of calibration standard were diluted with 100 µl of water for a curve of nominal concentrations 0.05 to 2.5 µg/ml to be injected onto the LC column. Quality control samples were prepared at nominal concentrations of low (0.05 µg/ml), medium (0.875 µg/ml), and high (2.5 µg/ml).

Preparation of Calibration Standards in Matrices and Quality Controls Samples.

Calibration standards were prepared by spiking into 50 µl of blank plasma, brain, or artificial cerebrospinal fluid (ACSF) to yield final concentrations of 0.05 to 2.5 µg/ml. Quality control (QC) samples were prepared in the same manner at concentrations of 0.05, 0.875, and 2.5 µg/ml for the low, medium, and high levels.

Artificial Cerebrospinal Fluid (ACSF) Sample Preparation. Due to the modest volume of CSF available from a mouse, i.e., approximately 5 µl per mouse, an ACSF was selected for development and calibration. The ACSF was composed of 126 mM NaCl, 2.5 mM KCl, 20 mM HEPES, 1.2 mM $NaH_2PO_4$, 25 mM $NaHCO_3$, 2.4 mM $CaCl_2$, and 1.2 mM $MgCl_2$ at pH 7. Calibration points were 50 µl of internal standards (IS) (1 µg/ml), 50 µl of calibration standard and the mixture then diluted with 100 µl of ACSF, yielding final concentrations of IS (0.5 µg/ml) and standard sample (0.05-2.5 µg/ml) such that 50% organic and 50% ACSF solution were injected onto the LC.

Plasma Sample Preparation. Mouse plasma samples, 50 µl, were transferred to a 1.5 ml centrifuge tube and then 50 µl of IS (4 µg/ml) and 50 µl of calibration standard sample were vortexed for 30 seconds. Acetonitrile (0.1 ml) was added to precipitate the proteins. After being vortexed for 3 minutes, the sample was centrifuged for 10 minutes at 13000 rpm. Supernatant (50 µl) was diluted with 50 µl water and injected onto the column.

Brain Sample Preparation.

Brain tissue (100 mg) was weighed and placed in a centrifuge tube. Methanol (100 µl) was added and the mixture was homogenized for 1 minute before adding 100 µl IS (6 µg/ml) to the homogenized mixture. The sample was then vortexed for 30 seconds before centrifuging for 10 minute at 13000 rpm. The supernatant liquid was diluted 50% with water and injected.

Method Validation.

The developed method was validated in terms of selectivity, linearity, lower limits of quantification (LLOQ), accuracy, precision, recovery, stability, and matrix effects according to established FDA guidelines.

Accuracy and Precision.

Intra-day accuracy was calculated using replicates (n=5) of 4, 8, and 15 at three concentrations 0.05, 0.875, and 2.5 µg/mL spiked into matrices during a single analytical session. The inter-day precision was also assessed by using replicates (n=5) of three concentrations made on three separate days.

Stability.

The stability of compounds 4, 8, and 15 was evaluated in ACSF, plasma, and brain matrices under various temperature and storage conditions. Stability at room temperature was studied by analyzing samples at 25° C. for 2 and 4 hours and stability at −80° C. was checked for one month. Samples were analyzed after three (−80° C. to 25° C.) freeze-thaw cycles. Stability studies were performed at three concentrations.

Matrix Effects Assessment.

Matrix effects were assessed with a post-column infusion method. A pump infused each analyte at low concentration at a constant rate into a T fitting post column. The spectrometer was set to SRM mode for that target. Sample preparations, without analyte, were resolved on the LC column.

Extraction Recovery.

The extraction recovery of each analysis was determined at the three concentrations low, mid, and high (0.05, 0.875, and 2.5 µg/ml) using the non-dosed ACSF, plasma, and brain samples. To determine the recovery, signals of spiked extracts from the blank ACSF, brain, and plasma were compared with that of injection of pure standards in mobile phase. IS recovery was determined for a single concentration of 0.5 µg/ml. Linearity and LLOQ A calibration curve was obtained from a plot of the peak area ratio (y) of each analyte to IS against plasma concentration (x) using weighted (1/x) least squares regression analysis.

Application to Pharmacokinetic Study and Data Analysis.

Using the validated LCMS/MS method, blood and brain levels of 4, 8, and 15 were measured in male and female C57BL6 mice (8-10 week-old, weighing approximately 25-30 grams). The mice were housed in a room with controlled temperature (23±3° C.) and moisture level (55±15% relative humidity) and exposed to a controlled 12 hour light/12 hour dark cycle. They were allowed to access to food and water ad libitum. Mice were fasted for 6 hours with free access to water prior to the pharmacokinetic study. To determine the time course of compounds 4, 8, and 15 action in the brain, the plasma pharmacokinetics and BBB penetration capability of the inhibitors were investigated. In these experiments, compounds 4, 8, and 15 were administered to mice by intravenous injection at a dosage of 10 mg/kg. Blood and brain samples were collected from mouse at each time point (2, 5, 10, 30, 60, 120, 240, 360, 720, 1440, and 2880 minutes), a total of 11 time points. For plasma measurements, blood (approximately 500-800 µl) was collected via cardiac-puncture into tubes containing sodium heparin anti-coagulant. Plasma was separated via centrifugation (4° C., 3500 rpm, 10 minutes) and stored in −80° C. freezer. For qualitative confirmations of these compounds in CSF, samples were collected at 2 time points (240 and 1440 min) from five animals at each time point. At the time of measurement, frozen plasma samples were thawed at room temperature and vortexed thoroughly. The following quantities were estimated using non-compartmental calculations performed with WINNONLIN 5.2 (Pharsight, Sunnyvale, Calif.): the area under the plasma concentration-time curve during the period of observation ($AUC_{0-\tau}$); the area under the plasma concentration-time curve from zero to infinity ($AUC_{0-\infty}$); the maximum plasma concentration ($C_{max}$); the time to reach $C_{max}$ ($T_{max}$); and the half-life ($t_{1/2}$).

Example 2

Molecular Dynamics and 3D QSAR Analysis

A total of 20 compounds were designed, and their capacity to inhibit Aβ-ABAD interaction was predicted using quantitative structure activity relationship studies, pre-ADME properties, docking studies and Comparative Molecular Field Analysis (CoMFA) analysis. The CoMFA was constructed by considering the following similarity descriptors; SlogP: Log of the octanol/water partition coefficient, an atomic contribution model (including implicit hydrogens); Density: Molecular mass density: Weight divided by vdw_vol (amu/Å3); SMR: Molecular refractivity, an atomic contribution model (including implicit hydrogens); Weight: Molecular weight (including implicit hydrogens) in atomic mass units; apol: Sum of the atomic polarizabilities (including implicit hydrogens); log P(o/w): Log of the octanol/water partition coefficient, a linear atomic model (including implicit hydrogens); logs: Log of the aqueous solubility (mol/L) calculated from an atom contribution linear atom type model; TPSA: Polar surface area (Å2) calculated using group contributions to approximate the polar surface area; vdw_vol: van der Waals volume (Å3) and rgyr: Radius of gyration.

The stabilized conformations obtained at the end of the molecular dynamics simulations were used to construct the database. For this database, molecule QSAR descriptors were calculated and graphs were plotted to analyze whether they were in the optimum range or not. Compounds 21-26 are violated drug-like properties, in particular with respect to molecular weight. The remaining compounds exhibited satisfactory values, indicating their potential as drug candidates.

The correlation plot generated from regression analysis showed a linear relationship among the training set of the compounds. The reliability of the QSAR model was further established by applying this model on the 20 test compounds and its predictive ability was evaluated. The correlation plot of the 20 test compounds not reliable as it included compounds 21-26. Upon removal of these compounds, the correlation plot of regression analysis showed a linear relationship for the final test data set.

The report of principal component analysis of QSAR fit showed the square root of the Eigen value of the covariance matrix corresponding to the principal component, i.e., the standard deviation of the data along the principal component vector (Table 3). The RMSE value was found to be zero and correlation coefficient ($R^2$) was 1. A 3D plot was constructed for the first three PCAs with activity field SlogP. All the data values were in the range of −3 to +3.

TABLE 3

| | |
|---|---|
| SlogP/SD(SlogP) | −7.09142 |
| dipole/SD(dipole) | +0.00000 |
| density/SD(density) | +0.00005 |
| SMR/SD(SMR) | +0.00933 |
| Weight/SD(Weight) | +1.46787 |
| apol/SD(apol) | −1.69396 |
| logP(o/w)/SD(logP(o/w)) | −0.01904 |
| logS/SD(logS) | −0.02588 |
| TPSA/SD(TPSA) | −1.89473 |
| vdw_vol/SD(vdw vol) | +1.07233 |
| lip_druglike/SD(lip_druglike) | +0.00000 |
| lip_violation/SD(lip_violation) | +0.00000 |
| rgyr/SD(rgyr) | +0.01576 |

SD, standard deviation

Example 3

ADME Predictions

The pharmacokinetic properties such as absorption, distribution, metabolism and excretion (ADME) describe how the body affects a specific drug after administration. ADME predictions of the 20 compounds indicated satisfactory results. Among the 20, compounds 4, 5, 6, 7, 8, 9, 10, 11, 12, 13, 14, 15, 16, 17, 21 and 24 exhibited good intestinal absorption, whereas compounds 22, 23, 25, and 26 exhibited moderate absorption. All compounds exhibited moderate permeability in Caco-2 cells and low permeability for MDCK cells. In vivo blood-brain barrier penetration capacity was predicted as exhibiting moderate absorption to the central nervous system (CNS) for compounds 4-17, whereas low absorption to CNS was observed for compounds 21-26. Blood brain barrier penetration is a crucial pharmacokinetic property because CNS-active compounds must pass across the BBB and CNS-inactive compounds should be impermeable to avoid CNS side effects.

Generally, the degree of plasma protein binding of any drug not only influences the drug action but also its disposition and efficacy. Usually, a drug that does not bind to plasma proteins will be available for diffusion or transport across cell membranes and finally interact with the target. For the compounds herein, the percent drug bound to plasma proteins was predicted and compounds 5, 8, 9, 10, 11, 12, 13, 14, 15, 16, 17 and 24 were predicted to bind strongly, whereas compounds 4, 6, 7, 21, 22, 23, 25, and 26 were predicted to bind weakly to plasma proteins. The predicted ADME properties and their values are shown in the Table 4.

TABLE 4

| Compound | [a]Abs (%) | [b]Caco-2 Perm. (nm/sec) | [c]MDCK Perm. (nm/sec) | [d]Plasma Protein Binding (%) | [e]Blood-Brain Barrier Penetration |
|---|---|---|---|---|---|
| 4 | 90.635 | 21.557 | 0.2484 | 83.69 | 0.2324 |
| 5 | 92.359 | 21.480 | 0.4673 | 91.89 | 0.4803 |
| 6 | 92.583 | 21.655 | 0.0732 | 88.53 | 0.4080 |
| 7 | 92.583 | 21.655 | 0.0732 | 88.12 | 0.4082 |
| 8 | 94.664 | 21.654 | 4.4672 | 97.01 | 0.2629 |
| 9 | 94.663 | 21.654 | 4.2637 | 100.00 | 0.2434 |
| 10 | 95.914 | 21.714 | 14.2191 | 100.00 | 0.3311 |
| 11 | 89.279 | 21.694 | 25.7699 | 100.00 | 0.1876 |
| 12 | 96.488 | 21.710 | 6.4507 | 100.00 | 0.1989 |
| 13 | 94.924 | 21.713 | 25.2219 | 100.00 | 0.3009 |
| 14 | 95.453 | 21.697 | 0.6218 | 96.40 | 0.3688 |
| 15 | 97.777 | 21.719 | 4.7661 | 100.00 | 0.6795 |
| 16 | 97.876 | 21.723 | 0.8251 | 98.20 | 0.9963 |
| 17 | 95.990 | 19.217 | 0.0218 | 100.00 | 0.3767 |
| 21 | 79.779 | 11.035 | 0.0436 | 87.56 | 0.0110 |
| 22 | 49.368 | 17.055 | 0.0434 | 78.52 | 0.0258 |
| 23 | 21.008 | 19.226 | 0.0434 | 60.27 | 0.0306 |
| 24 | 83.536 | 16.043 | 0.0436 | 90.71 | 0.0126 |
| 25 | 62.784 | 19.787 | 0.0447 | 81.16 | 0.0139 |
| 26 | 26.739 | 20.563 | 0.0434 | 66.55 | 0.0325 |

[a]Abs., human intestinal absorption was the sum of bioavailability and absorption evaluated from ratio of excretion or cumulative excretion in urine, bile and feces. Value between 0%-20% indicate poor absorption, 20%-70% moderate absorption and 70%-100% good absorption.
[b]Caco-2 Perm., in vitro Caco-2 cell permeability. Caco-2 cells are derived from human colon adenocarcinoma and possess multiple drug transport pathways through the intestinal epithelium. Values <4 indicate low permeability, 4-70 moderate permeability and >70 high permeability.
[c]MDCK Perm., in vitro MDCK cell permeability. MDCK cells are used for rapid permeability screening. Values <25 indicate low permeability, 25-500 moderate permeability and >500 high permeability.
[d]The percent of drug binding to plasma protein in vitro. Values <90% indicate weak binding and >90% indicate strong binding to plasma proteins.
[e]Blood-Brain Barrier (BBB) penetration is represented by BB = [Brain]/[Blood]. Values <0,1 indicate low absorption, 0.1-2.0 moderate absorption and >2.0 high absorption to CNS.

Example 4

Molecular Docking

Molecular docking of compounds 4-17 and 21-26 against the ABAD active site revealed that all of the compounds interacted with the ABAD active site with good docking scores dominated by hydrogen bonding and phosphonate salt-bridge formation (Table 5). Hydrophobic interactions also were observed to play a contributing role. The least and highest docking scores were found with the compound 24 and 26, respectively, but both of these compounds failed to show satisfactory QSAR descriptions and violated drug-like properties. Residues Ser 155 and Val 156 of the ABAD active site were found to play a predominant role in the interaction with all of the compounds. Lys 172 also exhibited arene interactions with compounds 7, 9, 16, and 21 due to the hydrophobicity of the ring structures, which in turn explains the strong interaction with ABAD. The docking scores and the bonding information with ABAD residues is tabulated and shown in Table 5.

TABLE 5

| Cmpd | Structure | Docking Score[a] | Number of Hydrogen Bonds[b] |
|---|---|---|---|
| 4 | 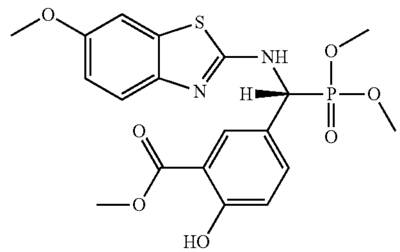 | −13.203 | 5, [Gln 115, Asn 121, Ser 155, Ala 158, Lys 172] |
| 5 | 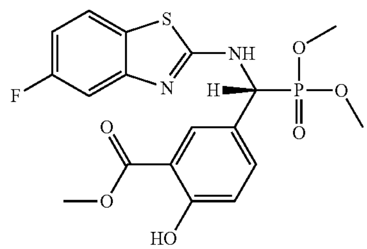 [SMILES: COC(=O)c1cc([C@H](Nc2nc3cc(F)ccc3s2)P(=O)(OC)OC)ccc1O] | −11.741 | 2, [Gln 115, Asp 119] |
| 6 | 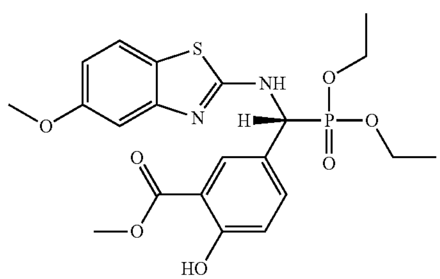 [SMILES: CCOP(=O)(OCC)[C@@H](Nc1nc2cc(OC)ccc2s1)c1ccc(O)c(C(=O)OC)c1] | −10.757 | 3 [Phe 114, Gln 115, Ser 155] |
| 7 | 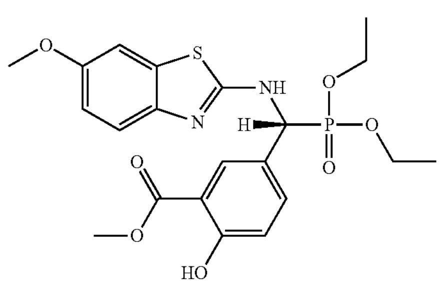 [SMILES: CCOP(=O)(OCC)[C@@H](Nc1nc2ccc(OC)cc2s1)c1ccc(O)c(C(=O)OC)c1] | −11.160 | Arene interaction [Lys 172] |
| 8 | 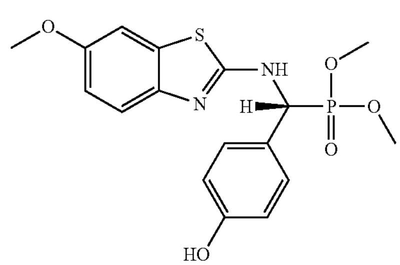 | −10.927 | 2 [Ser 155, Val 156] |

TABLE 5-continued

| Cmpd | Structure | Docking Score[a] | Number of Hydrogen Bonds[b] |
|---|---|---|---|
| 9 | 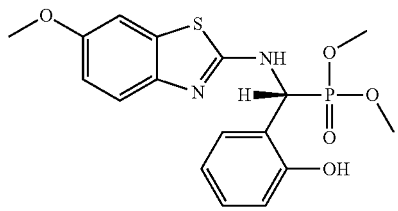 | −12.043 | 4 & Arene [Asn 121, Ser 155, Ser 155, Val 156] & [Lys 172] |
| 10 | 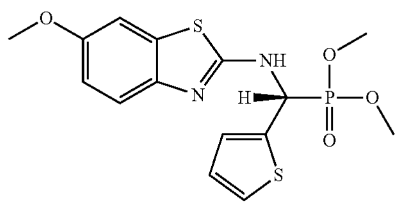 | −11.906 | 5 [Asn 121, Ser 155, Ser 155, Val 156, Lys 172] |
| 11 | 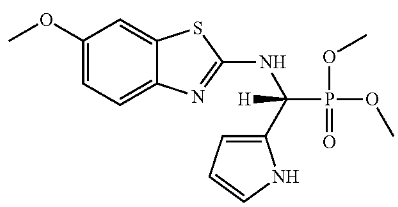 | −11.423 | 4 [Ser 155, Val 156, Lys 172, Lys 172] |
| 12 | 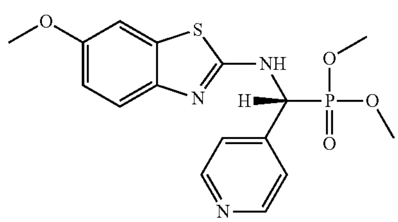 | −10.727 | 4 [Asn 121, Ser 155, Ser 155, Val 156] |
| 13 | 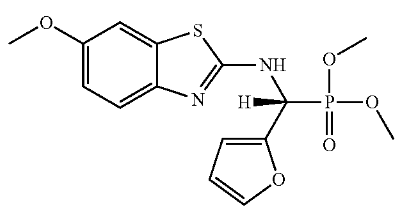 | −11.557 | 2 [Ser 155, Val 156] |
| 14 | 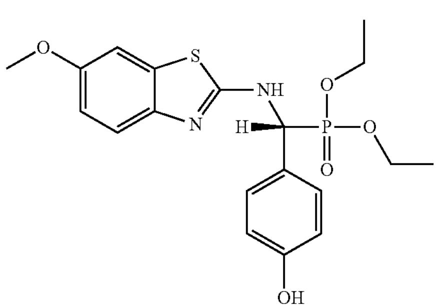 [SMILES: CCOP(=O)(OCC)[C@@H](Nc1nc2ccc(OC)cc2s1)c1ccc(O)cc1] | −10.623 | 1 [Gln 115] |

TABLE 5-continued

| Cmpd | Structure | Docking Score[a] | Number of Hydrogen Bonds[b] |
|---|---|---|---|
| 15 | 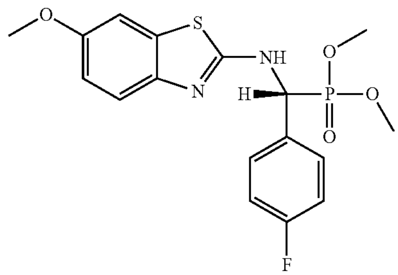 | -10.695 | 1 [Lys 172] |
| 16 | 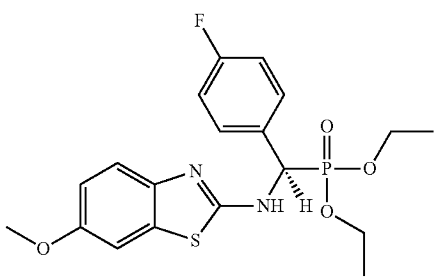 [SMILES: CCOP(=O)(OCC)[C@@H](Nc1nc2ccc(OC)cc2s1)c1ccc(F)cc1] | -10.990 | 2 & Arene [Ser 155, Val 156] & [Lys 172] |
| 17 | 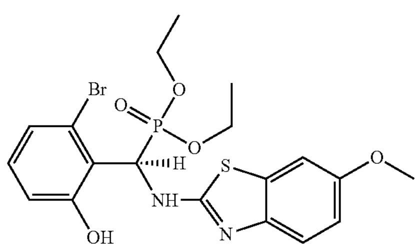 [SMILES: CCOP(=O)(OCC)[C@@H](Nc1nc2ccc(OC)cc2s1)c1c(O)cccc1Br] | -12.774 | 3 [Asp 119, Ser 155, Lys 172] |
| 21 | 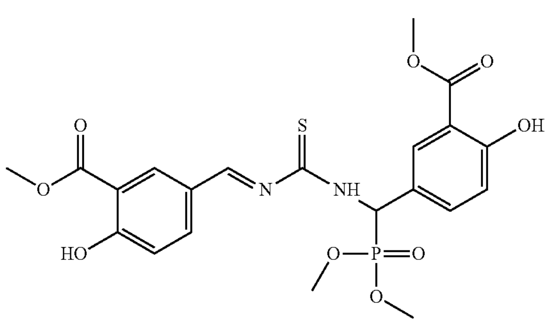 [SMILES: COC(=O)c1cc(/C=N/C(=S)NC(c2ccc(O)c(C(=O)OC)c2)P(=O)(OC)OC)ccc1O] | -11.616 | 2 & Arene [Gly 95, Ser 155] & [Lys 172] |
| 22 | 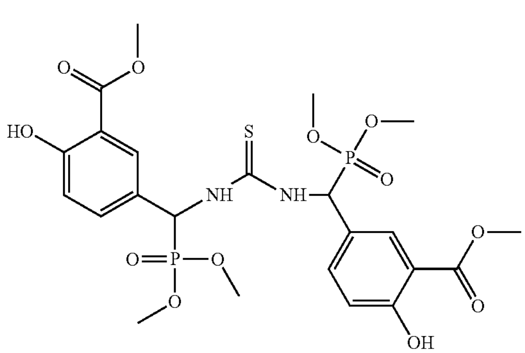 | -11.626 | — |

TABLE 5-continued

| Cmpd | Structure | Docking Score[a] | Number of Hydrogen Bonds[b] |
|---|---|---|---|
| 23 | 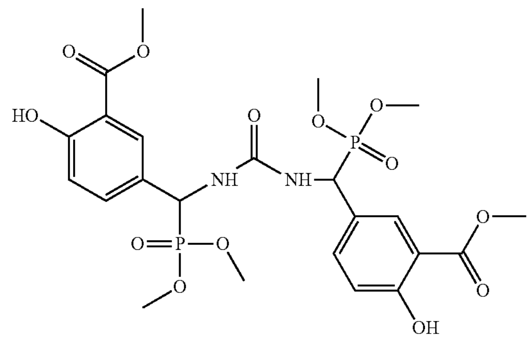 [SMILES: COC(=O)c1cc(C(NC(=O)NC(c2ccc(O)c(C(=O)OC)c2)P(=O)(OC)OC)P(=O)(OC)OC)ccc1O] | −11.785 | 5 [Gln 115, Asp 119, Asn 121, Ser 155, Lys 172] |
| 24 | 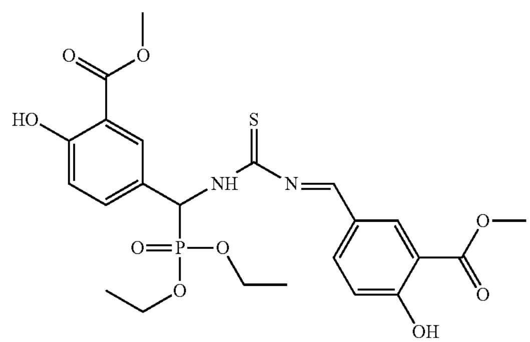 [SMILES: CCOP(=O)(OCC)C(NC(=O)/N=C/c1ccc(O)c(C(=O)OC)c1)c1ccc(O)c(C(=O)OC)c1] | −14.813 | 2 [Lys 172, Glu 160] |
| 25 | 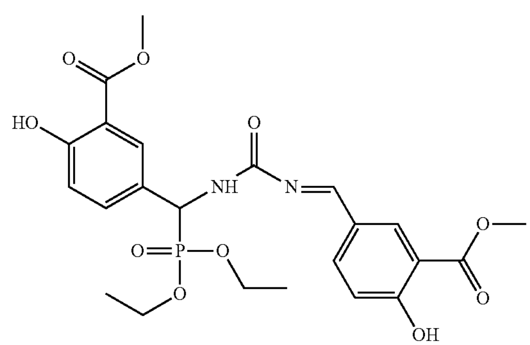 | −10.358 | 1 [Glu 160] |
| 26 | 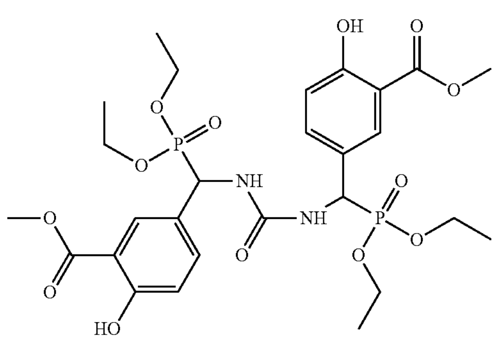 [SMILES: CCOP(=O)(OCC)C(NC(=O)NC(c1ccc(O)c(C(=O)OC)c1)P(=O)(OCC)OCC)c1ccc(O)c(C(=O)OC)c1] | −10.190 | 2 [Gln 115, Ser 155] |

[a]Docking scores generated during MOE docking between the lead compound and ABAD binding domain.

[b]Number of hydrogen bonds formed between the ABAD binding domain (residues of binding site indicated in brackets) and the lead compound.

Example 5

Biological Activity of ABAD Inhibitors

To confirm the inhibitory activity of the compounds, the ability of the compounds to inhibit reduction of SAAC by ABAD was determined. The results of this analysis are presented in Table 6.

TABLE 6

| Inhibitor | IC$_{50}$ (µM) | Ki (µM) | KD (nM) |
|---|---|---|---|
| 4 | 19.6 | 5.5 | 496 |
| 5 | 335.0 | 91.1 | 954 |
| 6 | 165.2 | 44.9 | — |
| 7 | 9.9 | 2.8 | 256 |
| 8 | 259.4 | 70.6 | — |
| 9 | 7.2 | 2.0 | 264 |
| 10 | 124.9 | 34.0 | — |
| 11 | 34.1 | 9.6 | 380 |

ABAD inhibitory activity of Compounds 4, 8 and 15 was further analyzed using in vitro surface plasmon resonance studies. To perform kinetic analyses of the binding of phosphonate derivatives to ABAD, the BIACORE 3000 instrument (based on surface plasmon resonance [SPR] technology) was used. The 1:1 Langmuir binding fit model was used for determining the equilibrium dissociation constant (KD), and the association (kon) and dissociation (koff) rate constants by using Equations (1) and (2).

$$dR/dt = kon \times C \times (Rmax - R) - koff \times R \quad (1)$$

Where R represents the response unit, C is the concentration of the analyte, and $$KD = koff/kon \quad (2)$$

The results were evaluated by $\chi2$ analysis. All the kinetic parameters are listed in Table 7.

TABLE 7

| ABAD Inhibitor | ABAD Enzymatic Activity | | SPR |
|---|---|---|---|
| | IC$_{50}$ (µM) | K$_i$ (µM) | KD (nM) |
| 4 | 341 ± 68.68 | 96.6 ± 19.4 | 496 |
| 8 | 52.7 ± 5.0 | 14.9 ± 1.4 | 291 |
| 15 | 1258.5 ± 198.6 | 355.5 ± 56.1 | 264 |

This analysis indicated that compound 8 exhibited the most potent inhibitory effect on SAAC reduction by ABAD with IC$_{50}$ at 52.7 µM and K$_i$ at 14.9 µM. Compound 4 showed a modest inhibitory effect on SAAC reduction and compound 15 did not inhibit SAAC reduction by ABAD at 10 µM; a slight inhibitory effect on SAAC reduction by ABAD was only observed at 100 or 400 µM. Because enzymatic activity of ABAD is essential for potentiation of Aβ cytotoxicity, these results indicate that blocking the Aβ-ABAD interaction with a small-molecule inhibitor can decrease Aβ induced cytotoxicity.

Mitochondrial Swelling in Response to Ca$^{2+}$.

Given that the Compounds 4, 8 and 15 could inhibit ABAD activity, it was determined whether these same compounds could decrease mitochondrial permeability transition pore (mPTP) formation. To demonstrate this effect, mitochondrial swelling assays were conducted. The results of this analysis indicated that the phosphonate derivatives antagonized calcium-mediated mitochondrial swelling. It was noted, however, that the ABAD inhibitors did not affect mitochondrial swelling without calcium, thereby indicating that there was no effect of these ABAD inhibitor on mitochondrial function.

Cytochrome C Oxidase (CcO) Activity.

Figure 1B:
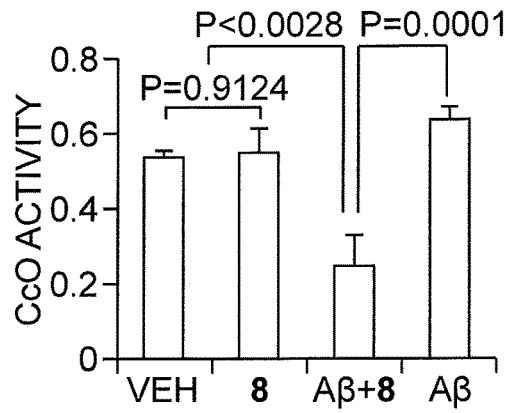
Figure 1C:
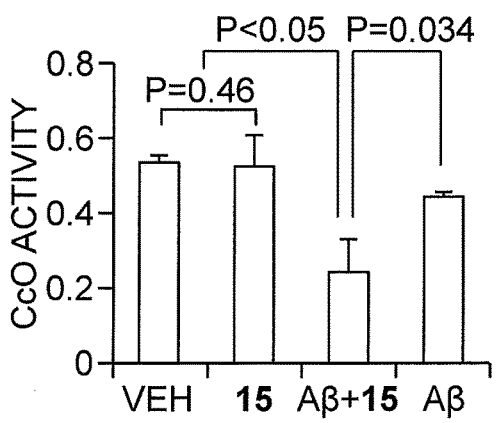

To assess the effect of ABAD inhibitor on Aft-induced mitochondrial respiratory function, CcO activity was determined. SK-N-SH cells were treated with 5 µM oligomer Aβ1-42 in the presence of 1 µM of Compound 4, 8 or 15 for 48 hours and CcO activity and ATP levels were measured. This analysis indicated that these ABAD inhibitors reversed the Aβ-mediated decrease of CcO activity (FIG. 1). Of note, the ABAD inhibitors alone had no effect on CcO activity without Aβ.

Adenosine-5'-triphosphate (ATP) Levels.

Figure 2A:
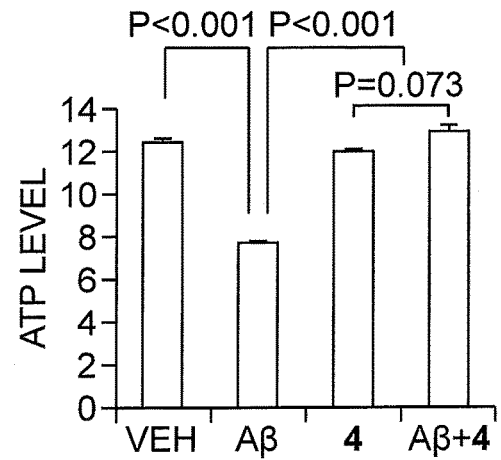
FIGS. 2A-2C show the effect of ABAD inhibitors, Compound 4 (FIG. 2A), Compound 8 (FIG. 2B), and Compound 15 (FIG. 2C), on Pip-impaired ATP levels. SK-NSH cells were exposed to 5 μM oligomer Aβ plus 1 μM indicated inhibitor; inhibitor alone; vehicle (VEH) without inhibitor; or Aβ alone. Forty-eight hour later, ATP levels (μmol mg$^{-1}$ protein) were measured in cell lysates.
Figure 2B:
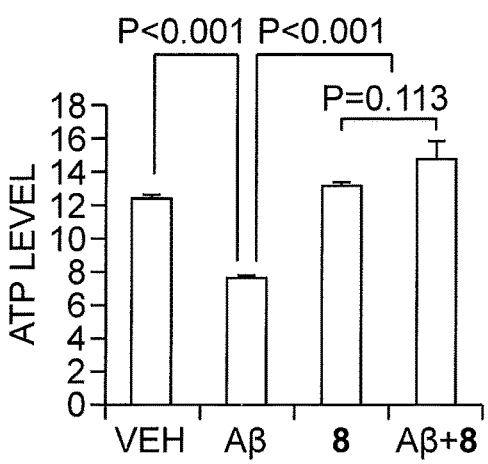
Figure 2C:
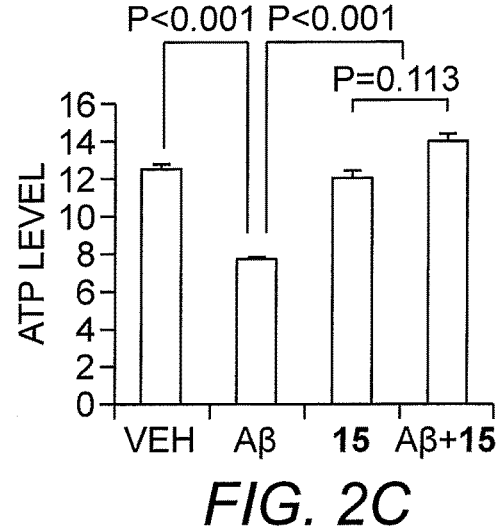

To determine the effect of ABAD inhibitors on Aβ-induced impairment in energy metabolism, ATP levels were measured. SK-N-SH cells were exposed to 5 µM Aβ1-42 in the presence of 1 µM of Compound 4, 8 or 15. ATP levels were measured in the cell lysates. As show in FIG. 2, Aβ treatment significantly decreased ATP levels, whereas the addition of ABAD inhibitors to the cells rescued ATP levels. ATP levels in the cells exposed to ABAD inhibitors were comparable to cells treated with vehicle alone without Aβ, indicating that the ABAD inhibitors did not exert an effect on mitochondrial energy metabolism. Therefore, ABAD inhibitors can block mitochondrial dysfunction mediated by Aβ.

It was of note that the substitution of methoxy at 6-position in benzothiazole amine had a positive impact on the bioactivity of the phosphonate derivatives, as evidenced by the results presented in (Table 7, FIG. 1-2), while substitution of the methoxy at the 5-position and fluoro at the 6-position of the benzothiazole ring had less of an effect. The presence of the hydroxyl group on benzene at 4-position had an impact on ABAD activity and substitution of the heterocyclic aldehyde at the amino position caused a loss of ABAD inhibitory activity. When the 4-hydroxy substituent was held constant, the methoxy substitution at the 6-position of benzthiazole amine was generally favorable for ABAD activity, conferring submicromolar IC$_{50}$ values.

Effect of ABAD Inhibitor on Cell Survival and Toxicity.

The effect of ABAD inhibitors on cell viability and toxicity was assessed using MTT reduction assay and trypan blue exclusion, which are widely used to assess cell survival and toxicity and to screen for drugs toxicity. Cells were treated with a range of concentrations of ABAD compound (4 and 8) at 1, 10, 50, 100 µM for 48 to 66 hours. Compared to vehicle treatment, cells treated with ABAD compounds did not exhibit decreased MTT reduction, increased percentage of trypan blue-positive cells or abnormal morphology. These data indicate that treatment of ABAD inhibitors alone does not have significant cytotoxicity.

Example 6

Pharmacokinetics and Ability to Cross BBB

Method Development.

During the development of a detection method for analytes 4, 8 and 15, multiple solvents were tested to find the optimal mobile phase. Compounds 4, 8 and 15 dissolved partially in water, but dissolved readily in methanol or acetonitrile. Acetonitrile was selected for better peak shape and compatibility with serum/brain protein precipitation. Compounds 8 and 15 were chosen as IS, because of their structural similarity. Selected reaction monitoring (SRM)

acquisitions were used for sensitivity and extended dynamic range. The cone voltage and collision energy were optimized for 4, 8 and 15 and the IS by continuously infusing a mixture of the two. The optimum cone voltage was 30V.

Matrix Effects.

There were no significant differences between the peaks generated by either the analytes extracted from the none-dosed ACSF, brain, and plasma or the analytes injected from water. The post-column infusion of 1 μg/ml 4, 8 or 15 showed no change of signal greater than 10% from sample matrix in their elution time windows.

Method Validation Selectivity.

Selectivity was evaluated by analyzing non-dosed ACSF, brain, and plasma from three different mice. Individual samples were analyzed using LC-MS/MS conditions to prevent interference with 4, 8 and 15 as well as IS. No other endogenous peaks could be detected other than our analyte peaks.

Linearity & LLOQ.

The calibration curves were constructed by plotting the IS peak area ratio for analytes 4, 8 and 15 against the concentrations of the IS (8 and 15). Each of the three calibrations curves (one for each matrix) were characterized by a linear segment and prepared in concentrations spanning 0.05-2.5 μg/ml. The LLOQ was 0.05 μg/ml from which a precision of <10% RSD was observed.

Accuracy and Precision.

The intra-day and inter-day accuracy and precision values were determined after analyzing five replicates at three separate concentration levels. Intraday accuracy for all three analytes ranged from 91.5% to 112.5% and contained a RSD range of 0.36% to 9.24%. All samples analyzed maintained a variability of <10% (RSD). These results support the accuracy, reliability, and reproducibility of our method.

Stability

The stability of ABAD compounds were determined under different temperature and storage conditions. 4, 8 and 15 standards were dissolved in methanol and were subjected short-term exposure at 25° C. for and 4 hours long-term storage conditions were assessed at −20° C. for twenty days. The displayed variability across all samples was less than 10% (RSD).

Pharmacokinetic Profile of Compounds 4, 8 and 15.

The LC-MS/MS method described above was used for the determination of 4, 8 and 15 in plasma, brain, and CSF for pharmacokinetic study. Based on the initial concentration data, the pharmacokinetic parameters including the area under the plasma concentration-time curve during the period of observation ($AUC_{0-t}$), the area under the plasma concentration-time curve from zero to infinity ($AUC_{0-\infty}$) the maximum plasma concentration ($C_{max}$) the time to reach $C_{max}$ ($T_{max}$) and the half-life ($t_{1/2}$) are shown in Table 8.

TABLE 8

| Compound | Matrix | $t_{1/2}$ (hours) | $T_{max}$ (hours) | $C_{max}$ (ng/mL) | $AUC_{0-48}$ (h * ng/mL) | $AUC_{0-\infty}$ (h * ng/mL) |
|---|---|---|---|---|---|---|
| 4 | Brain | 17.1 | 0.03 | 50.7 | 66.5 | 75.1 |
|   | Plasma | 6.2 | 0.03 | 2370.1 | 3027.8 | 3031.6 |
| 8 | Brain | 8.3 | 0.03 | 4.8 | 6.9 | 7.1 |
|   | Plasma | 5.5 | 0.03 | 2129.4 | 2862.6 | 2865.4 |
| 15 | Brain | 11.4 | 0.03 | 44.3 | 64.0 | 65.4 |
|   | Plasma | 6.1 | 0.03 | 1982.7 | 2983.9 | 2993.0 |

Figure 3A:
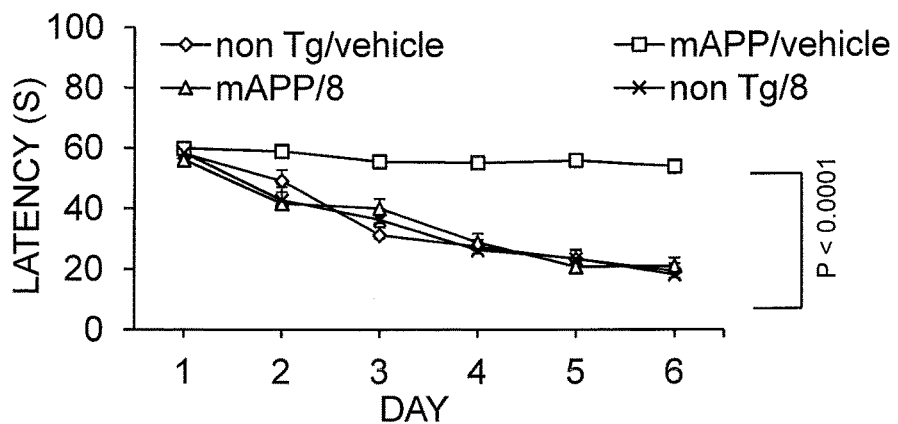
FIGS. 3A-3D show that Compound 8 improves learning memory in 6-months old Alzheimer's Disease (mAPP) mice. mAPP mice were administered Compound 8 (n=7) or vehicle (veh, n=6) by i.p. injection. Wild-type mice (Non Tg) were also administered Compound 8 (n=5) and vehicle (n=5). Each mouse was given four 60-second trials per day for six consecutive days to find the hidden platform in a Morris water maze. The recorded data were analyzed (FIG. 3A) and showed the changes of latency to find the hidden platform over 6 days of the training phase.
Figure 3B:
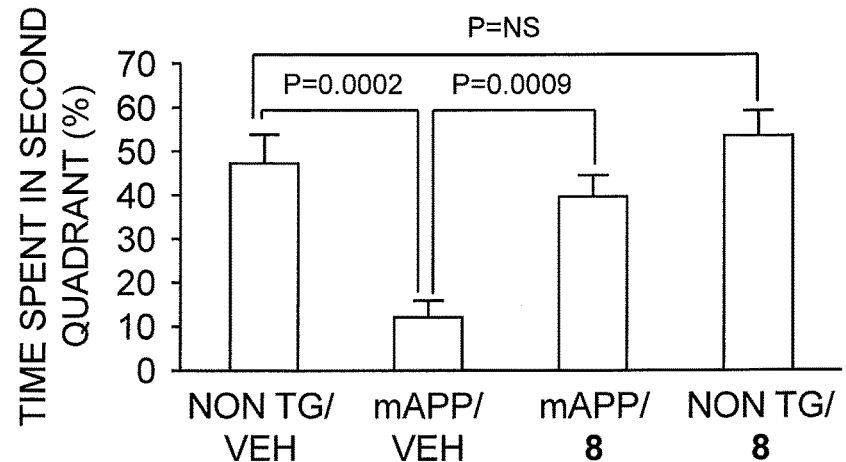
Figure 3C:
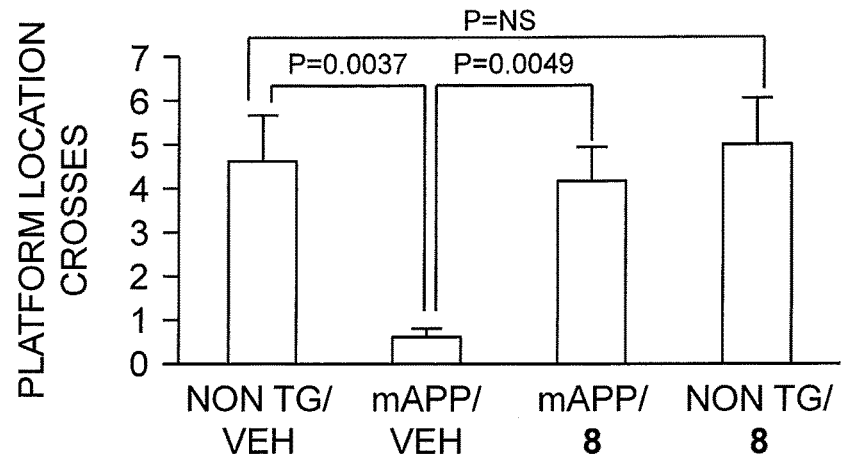
Figure 3D:
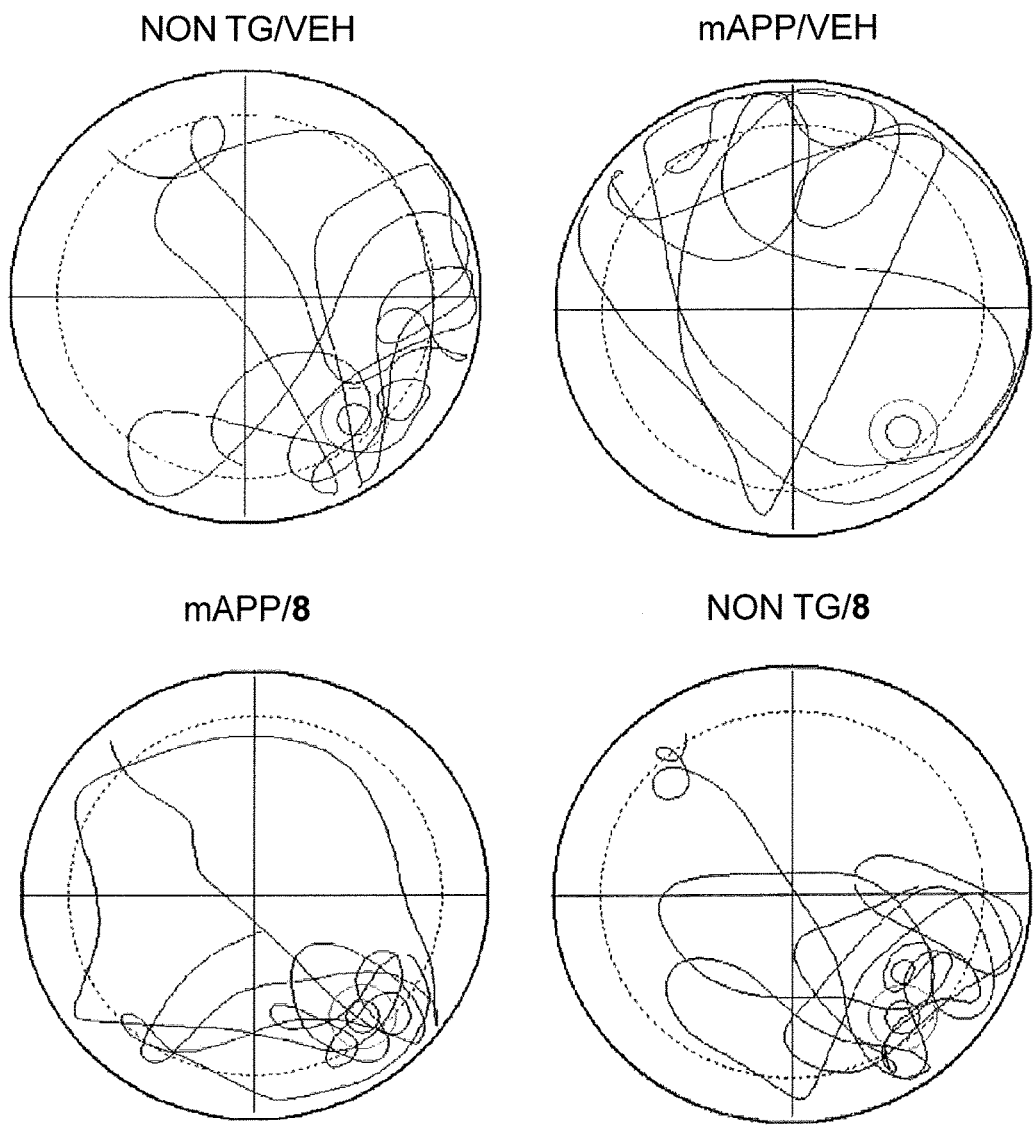
Figure 4A:
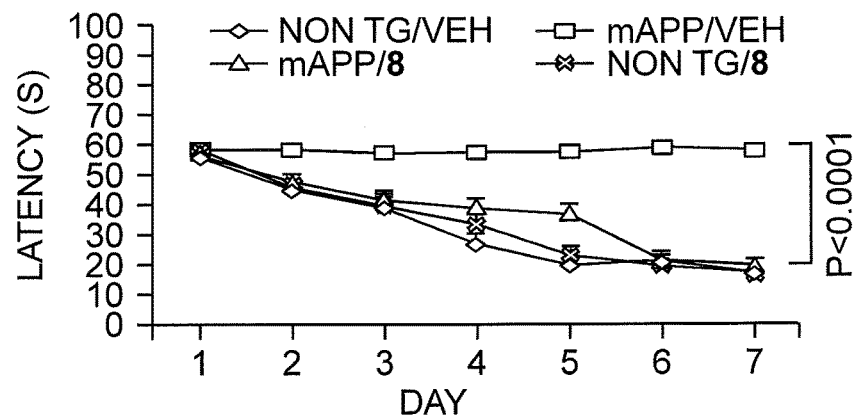
FIGS. 4A-4D show that Compound 8 improves learning memory in 9-14-months old mAPP mice. mAPP mice were administered with Compound 8 (n=12) or vehicle (n=10) by i.p. injection. Wild-type mice were also administered Compound 8 (n=9) and vehicle (n=9). Each mouse was given four 60-second trials per day for seven consecutive days to find the hidden platform in a Morris water maze. The recorded data were analyzed (FIG. 4A) and showed the changes of latency to find the hidden platform over 7 days of the training phase.
Figure 4B:
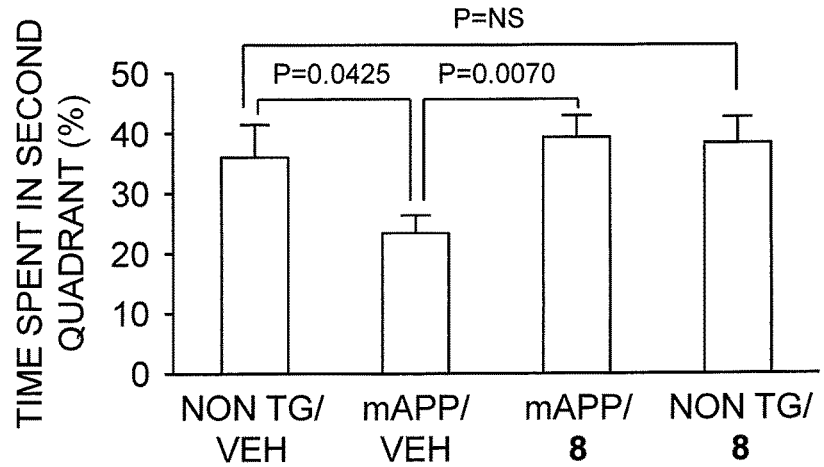
Figure 4C:
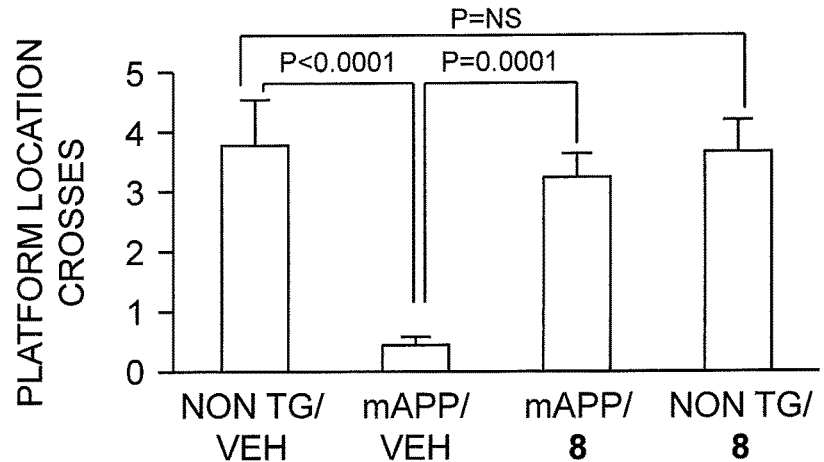
Figure 4D:
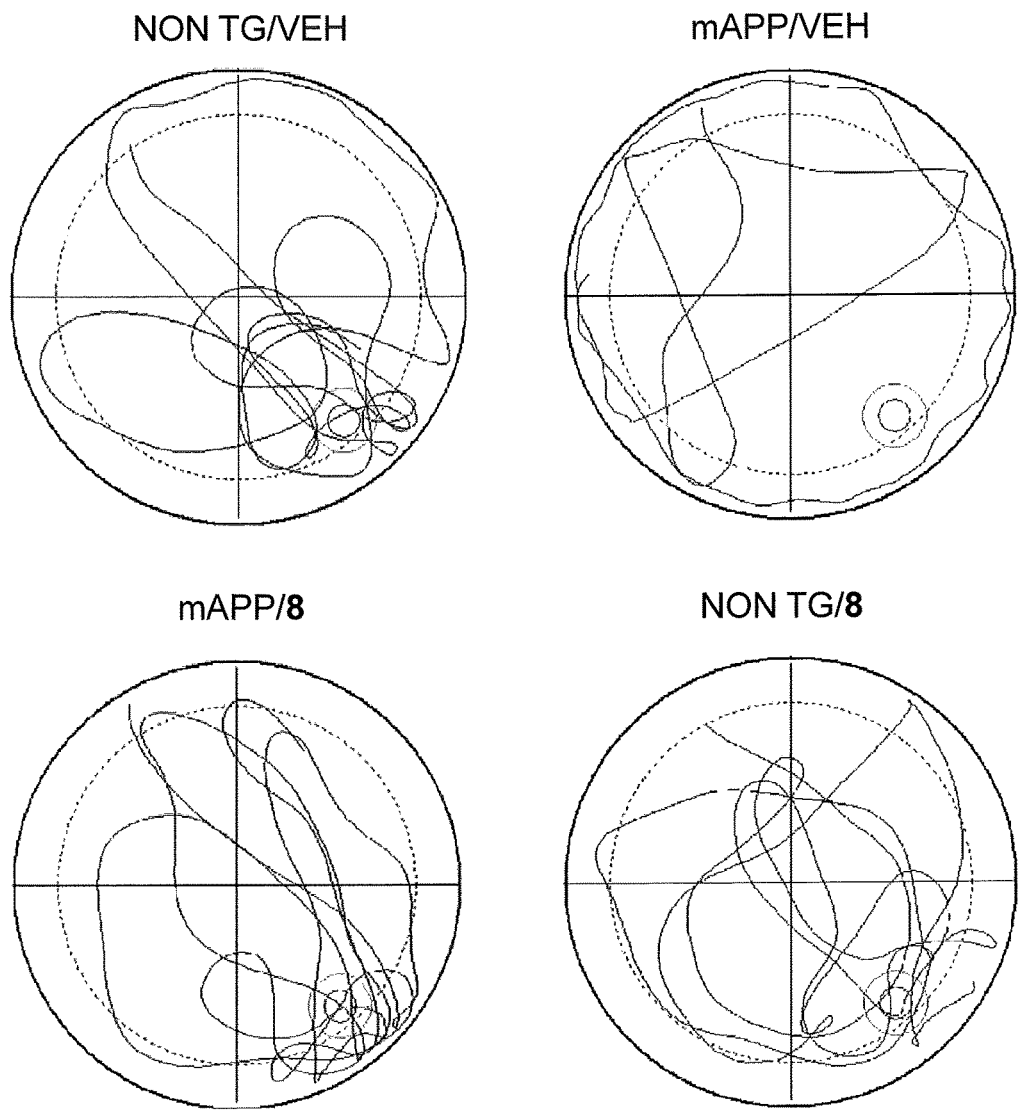
Figure 6A:
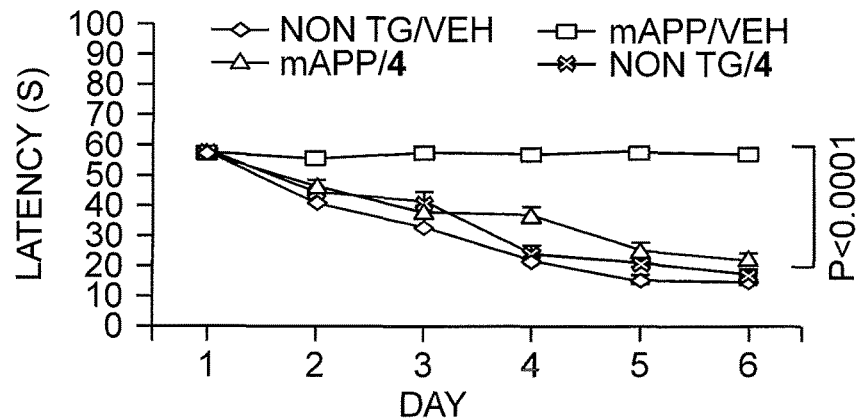
FIGS. 6A-6D show that Compound 4 improves learning memory in 9-months old mAPP mice. mAPP mice were administered Compound 4 (n=13) or vehicle (n=9) by i.p. injection. Non Tg were also administered Compound 4 (n=9) and vehicle (n=9). Each mouse was given four 60-second trials per day for six consecutive days to find the hidden platform in a Morris water maze. The recorded data were analyzed (FIG. 6A) and showed the changes of latency to find the hidden platform over 6 days of the training phase.
Figure 6B:
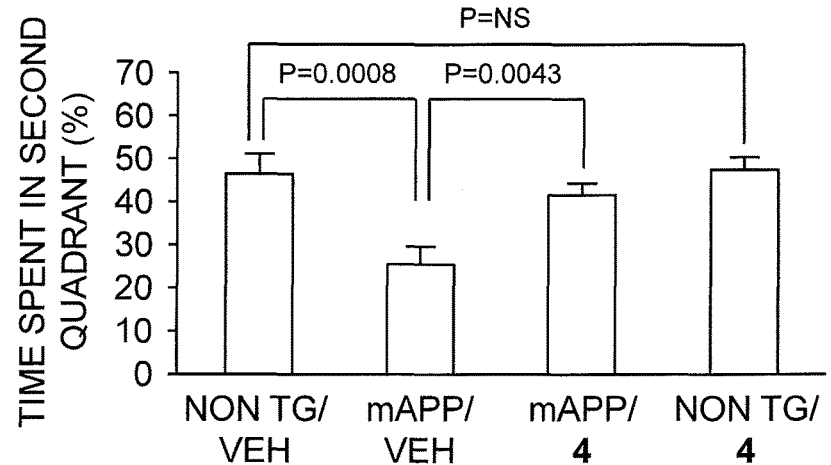
Figure 6C:
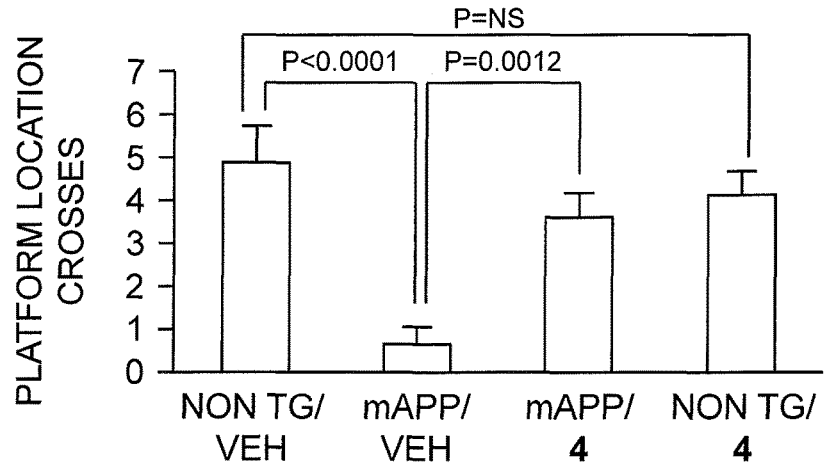
Figure 6D:
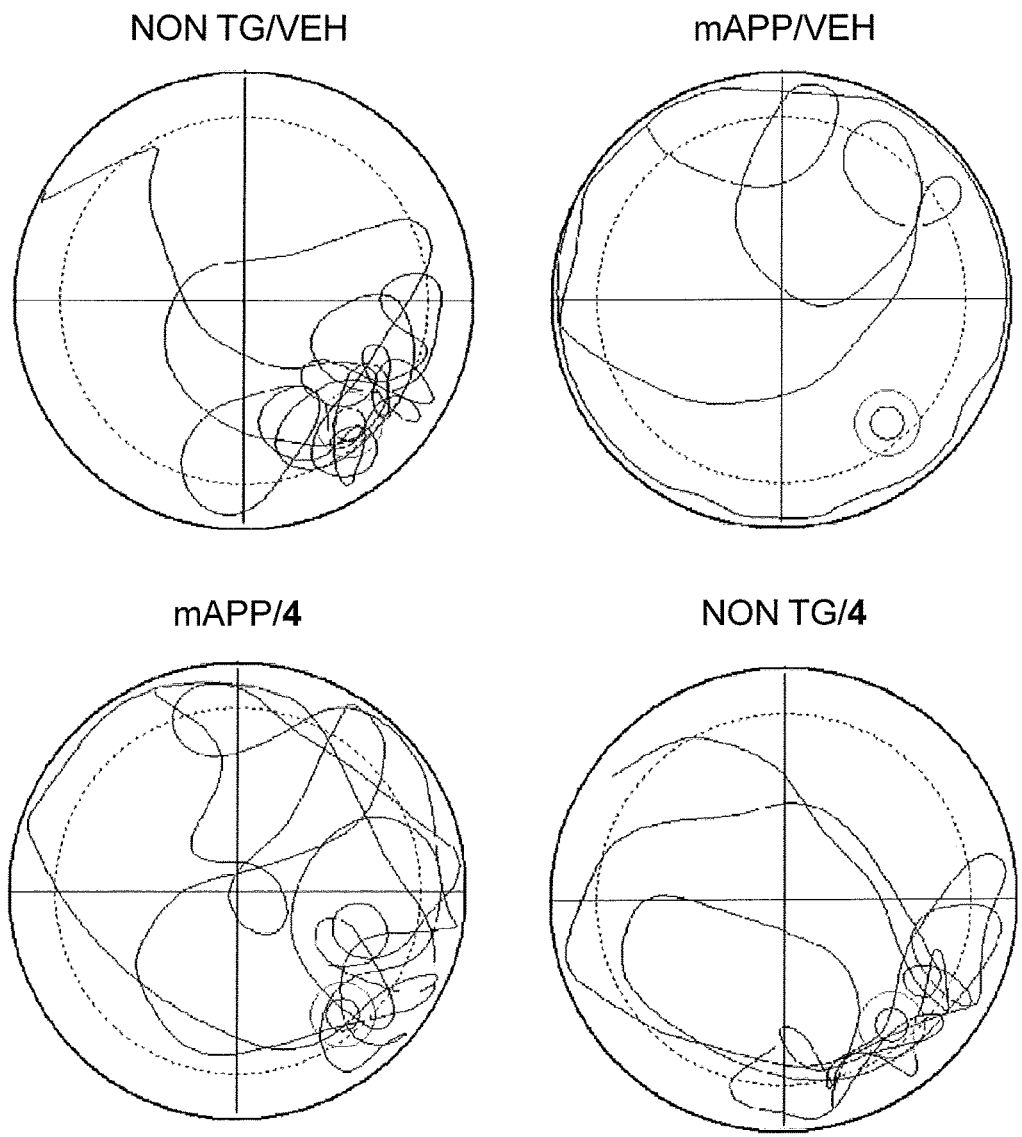

In addition, the effect of Compounds 4 and 8 on learning and memory of Alzheimer's Disease (AD) transgenic mice was evaluated. Six month and 9-14 month-old transgenic mice overexpressing a mutated form of the human amyloid precursor protein (mAPP mice) and their wild-type (non Tg) littermates were used in this study. In a non-spatial Morris water maze (MWM) task, AD mice treated with Compounds 4 and 8 displayed significantly shorter latency compared to untreated AD mice (FIGS. 3A, 4A and 6A). Moreover, performance in a spatial MWM trial was evaluated using crossings over the platform area (an index of memory precision; Morris (1984) *J. Neurosci. Methods* 11:47-60), percent of time spent in target quadrant (an index of memory retrieval; Morris (1984) *J. Neurosci. Methods* 11:47-60), and swim paths. This analysis indicated that the percent of time spent in the target quadrant (FIGS. 3B, 4B and 6B) and the number of crossings at the target location (FIGS. 3C, 4C and 6C) by mAPP mice treated with Compounds 4 and 8 were significantly more than untreated mAPP mice consistent with an improvement in memory retrieval and precision in the mAPP mice treated with Compounds 4 and 8. Representative swim paths showed that mAPP mice treated with Compounds 4 and 8 exhibited an improvement in the swim strategy used to locate the hidden platform (FIGS. 3D, 4D and 6D).

Figure 5A:
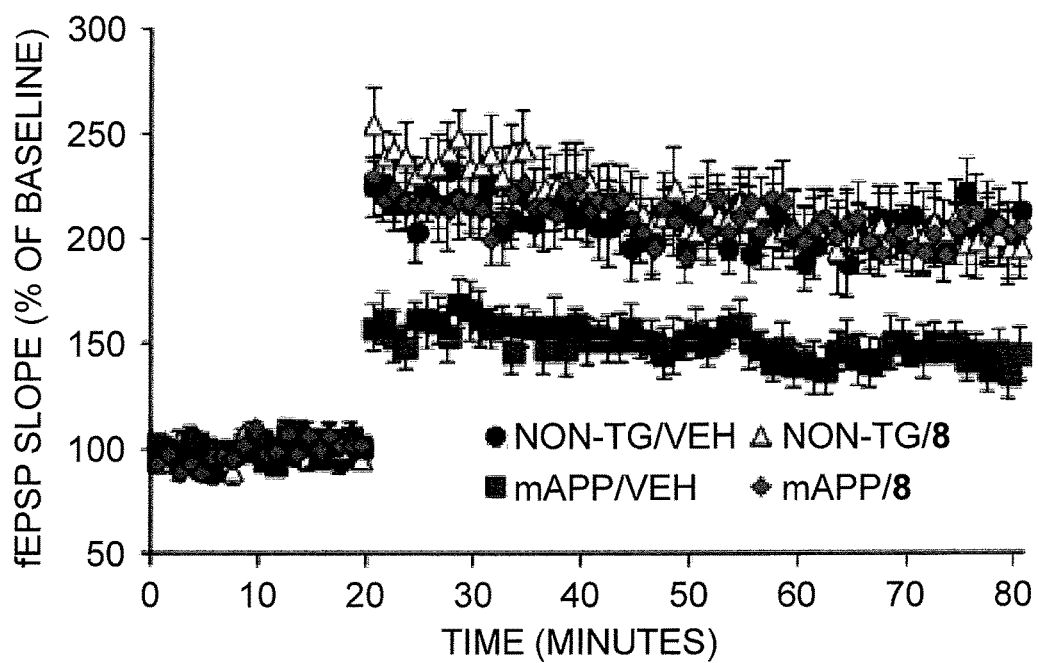
FIGS. 5A-5B show the protective effects of Compound 8 on hippocampal long-term potentiation (LTP) in mAPP mice. LTP was induced by theta-burst stimulation (TBS) 20 minutes after baseline recordings in hippocampal slices from Non-Tg mice treated with vehicle (n=9 slices from 3 mice), Non-Tg mice treated with Compound 8 (n=9 slices from 3 mice), mAPP mice treated with vehicle (n=8 slices from 3 mice), and mAPP mice treated with Compound 8 (n=8 slices from 3 mice). LTP is expressed as percentage potentiation of baseline (100%)(FIG. 5A).
Figure 5B:
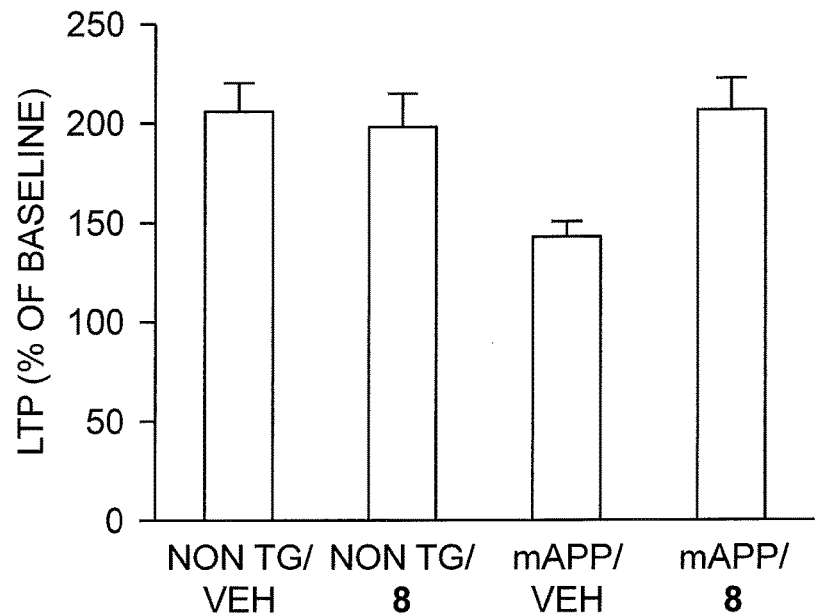
Figure 7A:
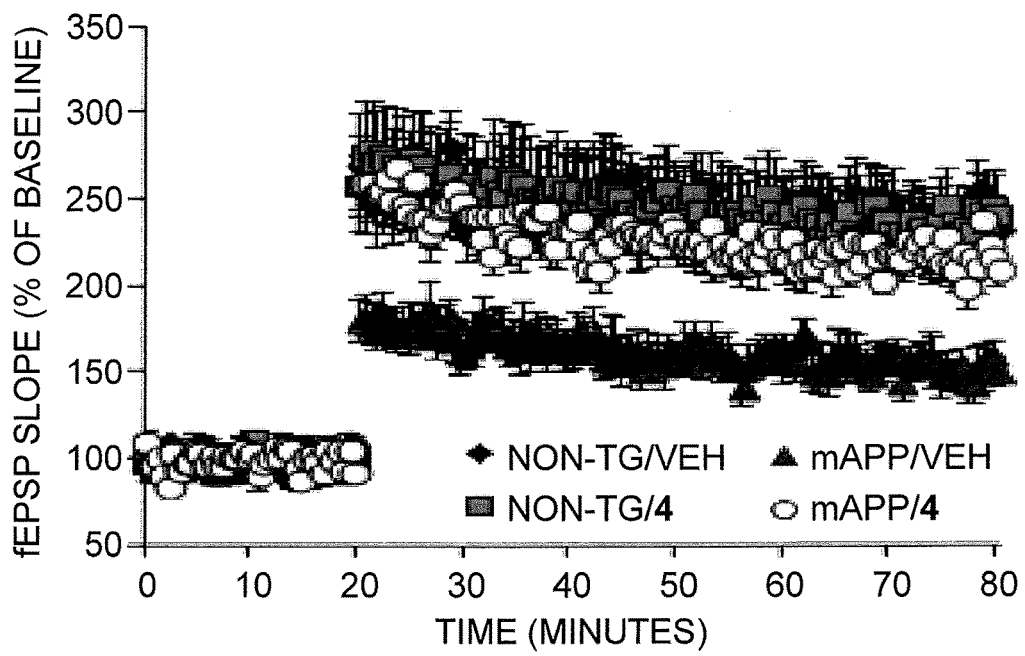
FIGS. 7A-7B show the protective effects of Compound 4 on hippocampal long-term potentiation (LTP) in mAPP mice. LTP was induced by theta-burst stimulation (TBS) 20 minutes after baseline recordings in hippocampal slices from Non-Tg mice treated with vehicle (n=8 slices from 3 mice), Non-Tg mice treated with Compound 4 (n=9 slices from 3 mice), mAPP mice treated with vehicle (n=8 slices from 3 mice), and mAPP mice treated with Compound 4 (n=9 slices from 3 mice). LTP is expressed as percentage potentiation of baseline (100%)(FIG. 7A).
Figure 7B:
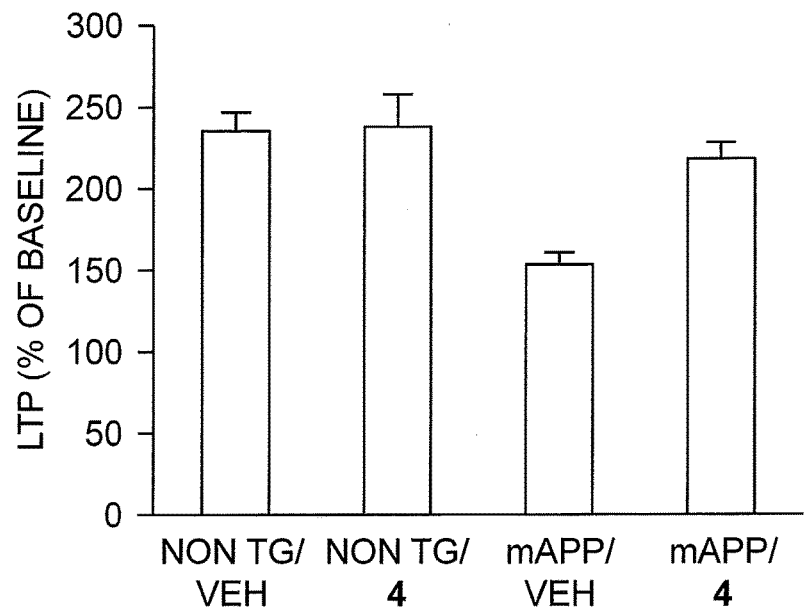

Synaptic failure in AD is largely reflected by impaired long-term synaptic plasticity in terms of long-term potentiation (LTP). To determine whether compounds of the invention improve long-term synaptic plasticity in mAPP mice, LTP was determined in hippocampal slices from Non-Tg and mAPP mice treated with vehicle or Compound 4 or 8. Representative field excitatory post-synaptic potentials (fEPSP) waveforms are provided in FIGS. 5A and 7A and the residual potentiation from fEPSP slopes occurring over the last 5 minutes of LTP recording are provided in FIGS. 5B and 7B. This analysis indicated that LTP was impaired in mAPP mice, but the impairments were diminished in mAPP mice treated with Compounds 4 and 8. Therefore, Compounds 4 and 8 provided protective effects in mAPP mice.

Figure 8:
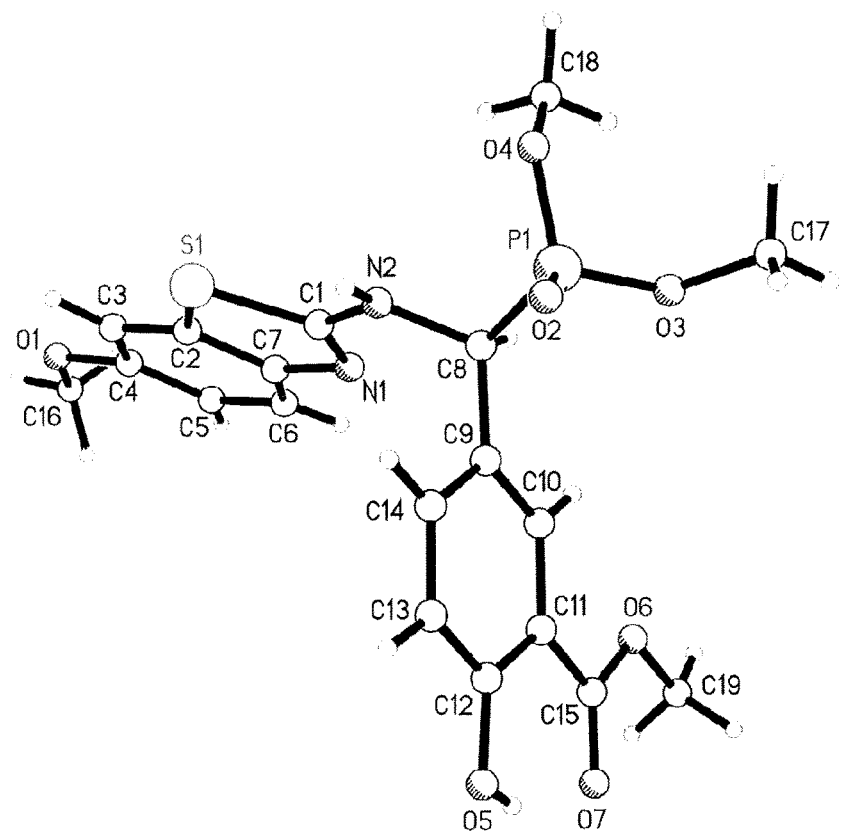
FIG. 8 shows the crystal structure for Compound 4 showing 50% probability displacement ellipsoids and atom-numbering scheme.
Figure 9:
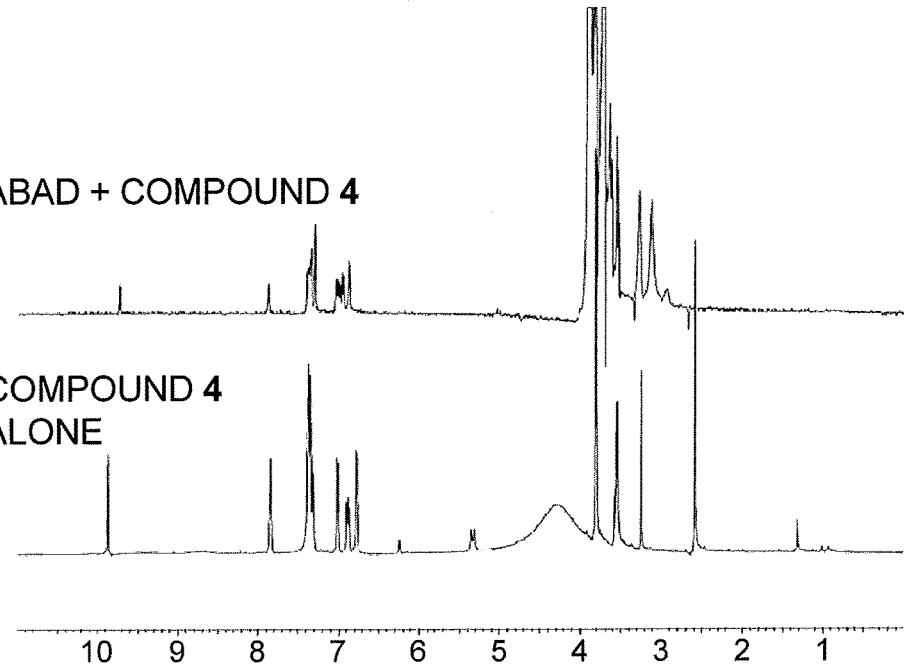
FIG. 9 shows the 1D-proton STD spectrum of ABAD (100 µM) in the presence of Compound 4 (10 µM) recorded at 600 MHz NMR and 298 K. (top). $^1$H reference spectrum of free ligand (bottom). The protein signals were eliminated in the STD spectrum by applying 25 ms spin lock filter.
Figure 10:
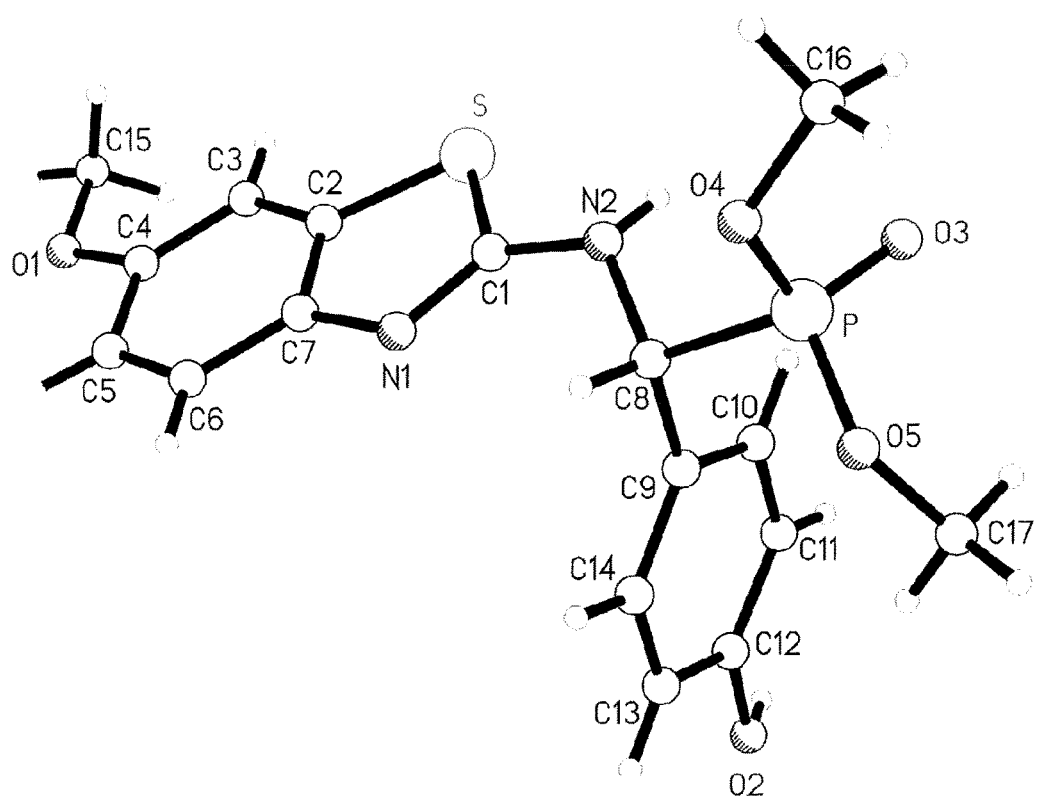
FIG. 10 shows the crystal structure for Compound 8 showing 50% probability displacement ellipsoids and atom-numbering scheme.
Figure 11:
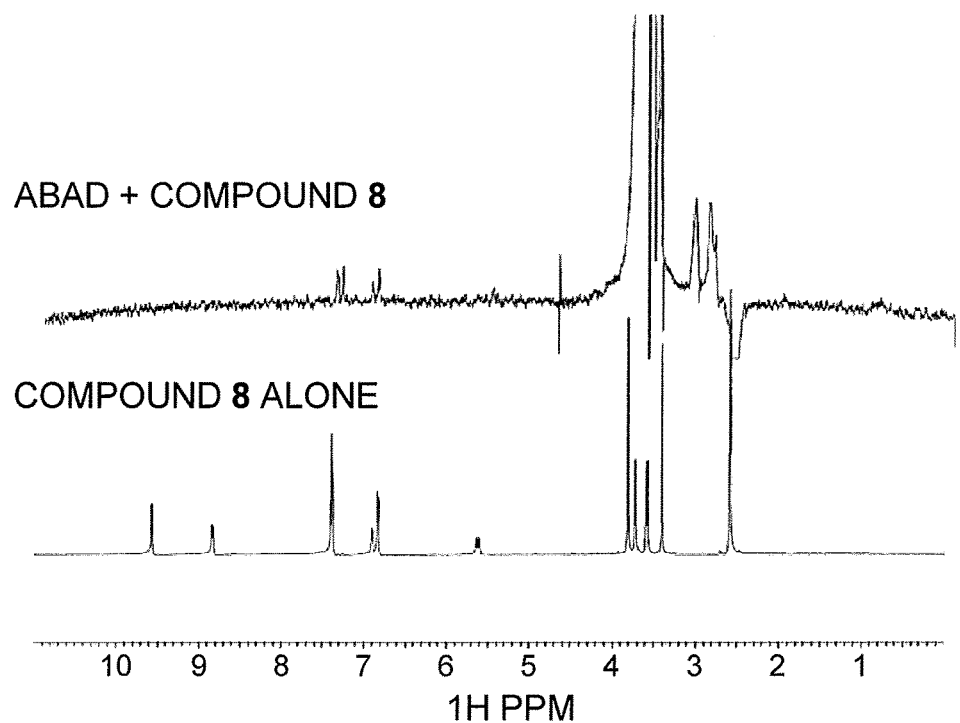
FIG. 11 shows the 1D-proton STD spectrum of ABAD (100 µM) in the presence of Compound 8 (10 µM) recorded at 600 MHz NMR and 298 K. (top). $^1$H reference spectrum of free ligand (bottom). The protein signals were eliminated in the STD spectrum by applying 25 ms spin lock filter.

Crystal structure analyses of Compounds 4 and 8 are presented in FIGS. 8 and 10, respectively. Further, to analyze binding, saturation transfer difference (STD) experiments (Mayer & Meyer (1999) *Angew Chem. Int. Ed. Engl.* 38:1784-1788) were performed with ABAD in the presence of Compounds 4 and 8 (FIGS. 9 and 11, respectively). The STD approach monitors the 1D proton spectrum of a small molecule in the presence of a substoichiometric amount of unlabeled protein and provides an indication of which atoms are in close contact to the protein, i.e., those atoms that are closer to the protein will have more intense signals owing to a more efficient saturation transfer.

What is claimed is:

1. A compound of Formula II, or an analog, stereoisomer, tautomer, pharmaceutically acceptable salt, or prodrug thereof,

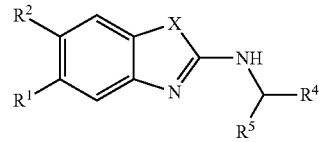

Formula II wherein
X is S or O;
one of $R^1$ or $R^2$ is a halo, alkoxyl, hydroxyl or methylcarboxylate group and the other of $R^1$ or $R^2$ a hydrogen, hydroxyl, halo, alkoxy, or methylcarboxylate group;
$R^4$ is a phosphonate group; and
$R^5$ is a substituted or unsubstituted aryl or substituted or unsubstituted heteroaryl group, wherein said substituted aryl or substituted heteroaryl comprises one or two substituents selected from the group of —$NO_2$, —CN, —$NH_2$, —COOH, —OH, —$OCH_3$, —$OCF_3$, —$CONH_2$, -alkyl, -alkoxy or a methylcarboxylate group.

2. The compound of claim 1, wherein X is S; $R^1$ is H; $R^2$ is alkoxy; $R^4$ is a phosphonate group having the structure —$PO(OR^7)_2$, wherein each $R^7$ is a methyl group; and $R^5$ is an aryl substituted with an —OH, methylcarboxylate group or a combination thereof.

3. A pharmaceutical composition comprising the compound of claim 1 and a pharmaceutically acceptable carrier.

4. A method for inhibiting the activity of Amyloid Binding Alcohol Dehydrogenase (ABAD) comprising contacting ABAD with a compound of claim 1 thereby inhibiting the activity of ABAD.

5. A method for ameliorating or treating Alzheimer's Disease comprising administering to a subject in need thereof the pharmaceutical composition of claim 3 thereby ameliorating or treating the subject's Alzheimer's Disease.

* * * * *